United States Patent [19]

Catsimpoolas et al.

[11] Patent Number: 4,888,324

[45] Date of Patent: Dec. 19, 1989

[54] METHOD FOR ENHANCING ANGIOGENESIS WITH LIPID CONTAINING MOLECULES

[75] Inventors: Nicholas Catsimpoolas, Newton Centre; Robert McCluer, Acton, both of Mass.; Robert S. Sinn, New York, N.Y.; James Evans, Winchester, Mass.

[73] Assignees: Angio-Medical Corporation, New York, N.Y.; Trustees of Boston University, Boston, Mass.

[21] Appl. No.: 116,014

[22] Filed: Nov. 2, 1987

Related U.S. Application Data

[63] Continuation of Ser. No. 782,724, Oct. 1, 1985, Pat. No. 4,710,490.

[51] Int. Cl.[4] .................... A61K 31/70; A61K 31/685
[52] U.S. Cl. .......................................... 514/25; 514/78; 514/557; 514/558
[58] Field of Search .................... 514/25, 78, 557, 558

[56] References Cited

U.S. PATENT DOCUMENTS

| | | | |
|---|---|---|---|
| 1,741,786 | 12/1929 | Magat et al. | 514/78 |
| 4,252,793 | 2/1981 | Altman | 514/78 |
| 4,710,490 | 12/1987 | Catsimpoolas et al. | 514/25 |

FOREIGN PATENT DOCUMENTS

| | | | |
|---|---|---|---|
| 1082374 | 3/1984 | U.S.S.R. | 514/78 |
| 2002631 | 2/1979 | United Kingdom | 514/78 |

OTHER PUBLICATIONS

Chem. Pharm. Bull., 31(7): 2209–2217 (1983).

Primary Examiner—John W. Rollins
Attorney, Agent, or Firm—Felfe & Lynch

[57] ABSTRACT

Compositions which contain lipid containing molecules possessing angiogenic activity are disclosed. The lipid containing molecules have been found in mammalian tissue, particularly the omentum, of various animals. Additionally, known lipids, such as gangliosides, are unexpectedly found to possess angiogenic activity. A method for obtaining the omentum-derived lipids, and for use of these and known lipids, are disclosed as well.

22 Claims, 20 Drawing Sheets

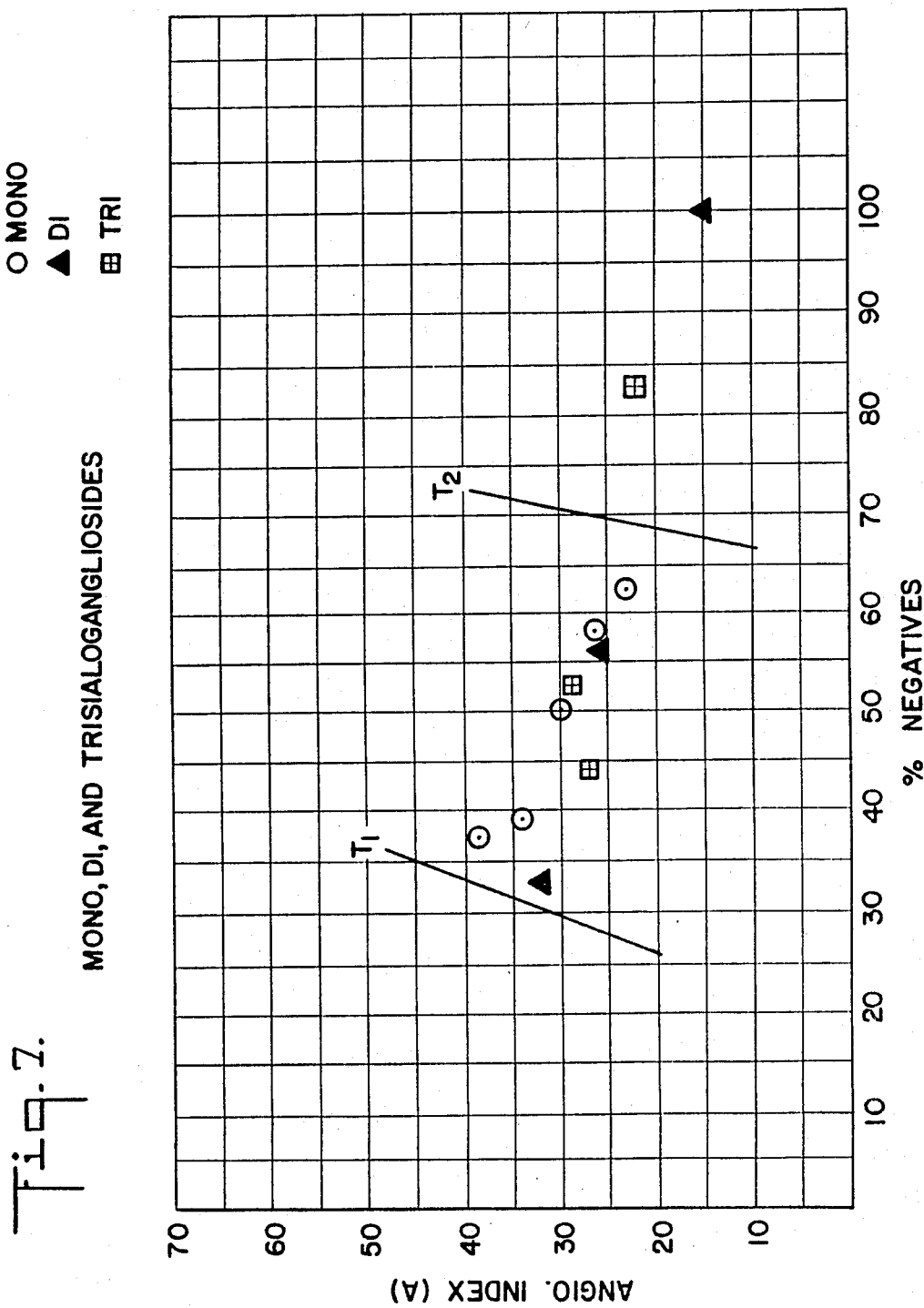

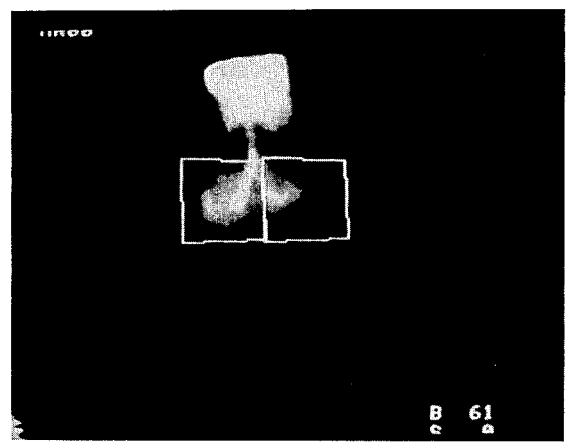
72 Hours
Right Leg
232288 cpm
Left Leg
179831 cpm
29.6% increase
Fig. 18.

6 Days (post op)
RIGHT LEG            LEFT LEG
159,000 cpm           115,000 cpm
38.2% increase Day 9
RIGHT LEG            LEFT LEG
95909 cpm           57831 cpm
65.8% increase Fig. 22.
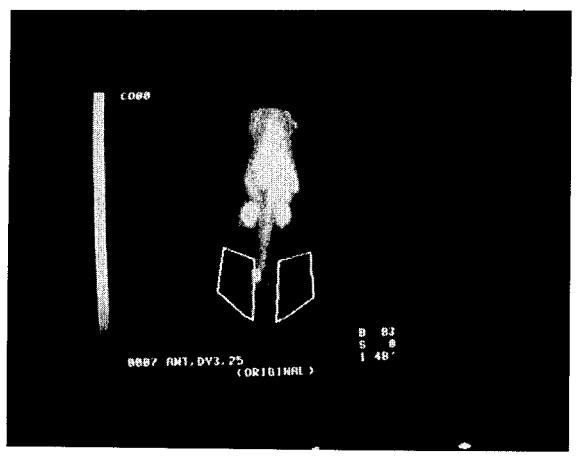
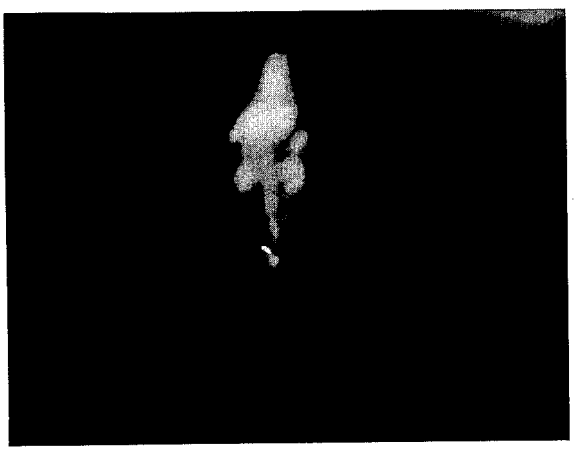
Fig. 23.
Fig. 24.
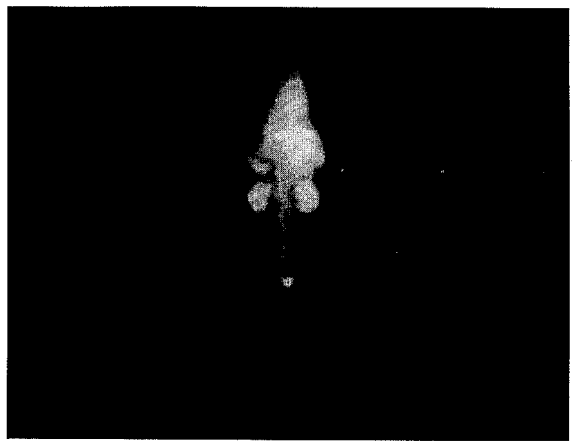

METHOD FOR ENHANCING ANGIOGENESIS WITH LIPID CONTAINING MOLECULES

This is a divisional of Ser. No. 782,724, filed Oct. 1, 1985, now U.S. Pat. No. 4,710,490.

FIELD OF THE INVENTION

This invention relates to lipid containing compositions, which possess enhanced angiogenic properties.

PRIOR ART

Angiogenesis is the process by which new blood vessels are formed, with accompanying increased blood circulation. The field of angiogenesis has been a favorite for research and investigation for over one hundred years. See, e.g., Virchau, R., *Die Krankhaftern Geshwulste*, Hirshwald, Berlin (1863); Thiersch, C., *Die Haut Mit Atlas*, Leipzig (1865); (significance of the interaction between host vasculature and survival and growth of solid malignant tumors observed). Interest has been fueled by the observation that angiogenic factors are found, in trace amounts, in normal tissue. See, e.g., D'Amore et al., PNAS 78:3068-3072 (1981); Kissun, et al., *Br.J.Ophthalmol.* 66:165-169 (1982); (retinal tissue); DeCarvellho, et al., *Angiology* 34:231-243 (1983); (activated lymphocytes and macrophages); Frederick, et al., *Science* 224:289-390 (1984); (human follicular fluid); Burgos, *Eur.J.Clin.Invest.* 13:289-296 (1983); (amniochondrion and placenta); Catellot, et al., PNAS 79:5597-5601 (1982); (culture medium of 3T3 cells). The trace amounts of angiogenic factors observed in these tissues do not, however, show any angiogenic activity other than in normal growth and development of tissues and organs. Similarly, angiogenic factors have been observed in tissues of pathological origin. See, e.g., Weiss, et al., *Br.J.Cancer* 40:493-496 (1979); Fencelau, et al., *J.Biol.Chem.* 256:9605-9611 (1981), McAslau, et al., *Exp.Cell Res.* 119:181-190 (1979); (tumor cells); Kumar, et al., *Lancet* 2:364-367 (1983); Brown, et al., *Lancet* 1:682-685 (1980) (synovial fluid of arthritis patients); Hill, et al., *Experientia* 39:583-585 (1983) (vitreous material of diabetics); Banda, et al., *PNAS* 79:7773-7777 (1982) (wound fluid).

Goldsmith et al, *JAMA* 252:2034-2036 is the first report of an angiogenic factor which shows activity beyond normal growth and development, and large amounts of the factor. The factor was found in chloroform/methanol fractionates of feline omenta (CMFr). See U.S. Pat. No. 4,699,788 entitled "Angiogenesis Factor and Method for Producing Angiogenesis," of Catsimpoolas and Goldsmith. This application is incorporated by reference herein.

It has now been found that the crude lipid extract of Goldsmith et al. may be purified into various fractions which possess angiogenic properties far above those observed in the CMFr.

Additionally, it has been found that commercially available gangliosides such as gangliosides derived from brain tissue and other lipid containing compounds also possess angiogenic properties. Further, it has been found that new compositions of known lipid containing compounds may be formed which also possess angiogenic properties.

The discovery of lipid containing compounds which possess angiogenic properties is new to the art. Previously attention had been focused on proteinaceous angiogenic factors. See, e.g., Kumar et al., *Lancet II*:3-64-367 (1983) (proteinaceous factors from 300 to $10^5$ daltons); Kissun, et al., *supra* (proteinaceous factors up to 70 kd); Banda, et al., *supra* (proteins of about 2-14 kd); Burgos, et al., *supra*, (protein complexes of from 100-200 kd). It has now been unexpectedly shown that compositions containing lipid containing molecules, such as gangliosides, glycolipids, ceramides, cerebrosides, phospholipids, sphingosides, and so forth, exhibit enhanced angiogenic activity.

SUMMARY OF THE INVENTION

Lipid containing compositions which are derived from mammalian sources and which have angiogenic properties are described. In addition, new compositions, comprising mixtures of old, lipid containing compounds, which also possess angiogenic properties, are disclosed. Yet further, it is disclosed that known lipid containing compositions have unexpected angiogenic properties.

BRIEF DESCRIPTION OF THE FIGURES

FIG. 3 shows further the additional fractions obtained by the methods described infra.

FIGS. 6-17 are graphic illustrations of linear categorization studies based upon the CAM assays of the invention.

FIGS. 18-24 are photographs and graphic representation of in vivo revascularization studies performed using the CMFr.

DETAILED DESCRIPTION OF PREFERRED EMBODIMENTS

Figure 1:
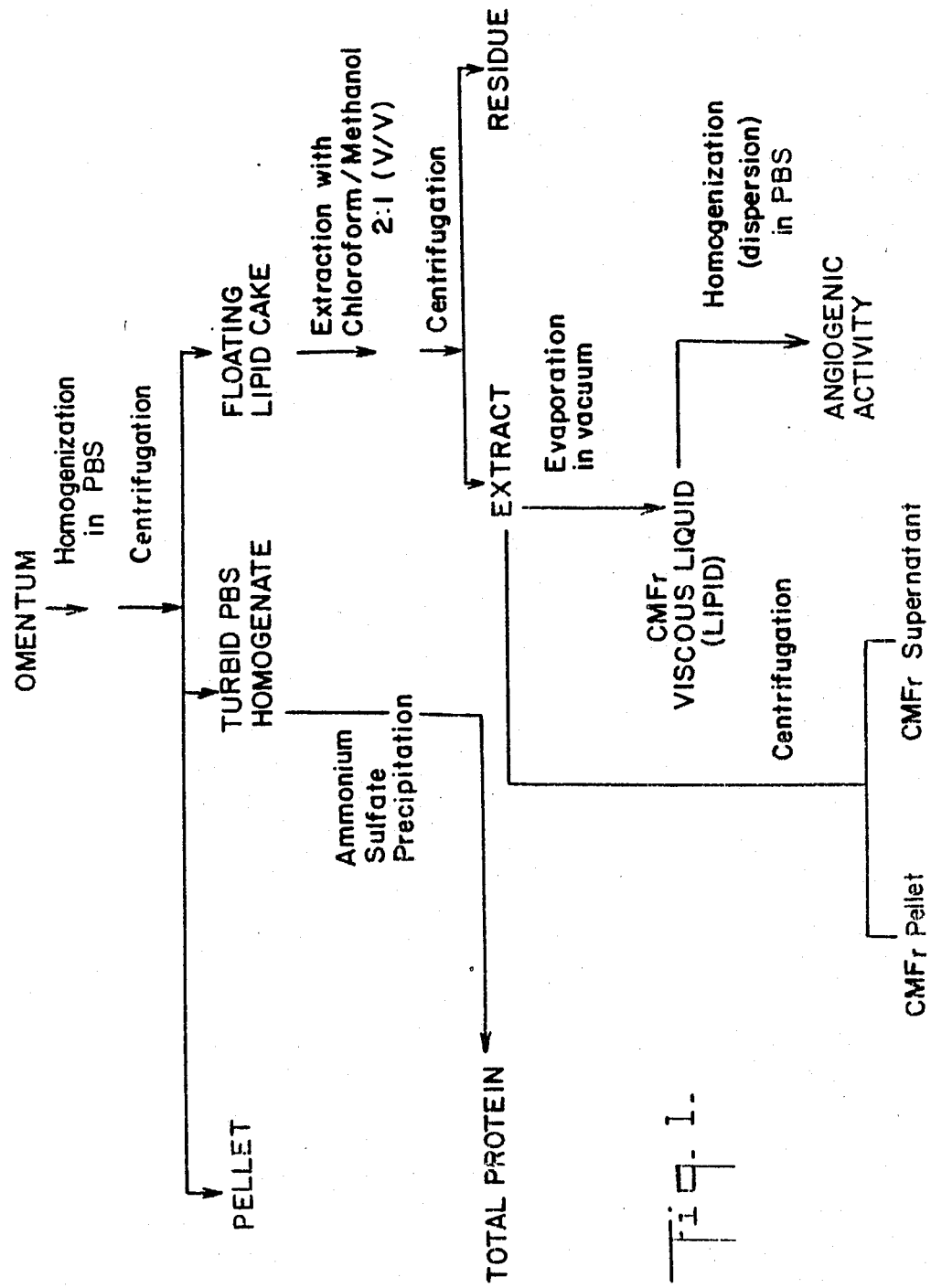
FIG. 1, which is also disclosed in U.S. Pat. No. 4,699,788, depicts a method for obtaining CMFr.

I. Obtaining the Chloroform Methanol Lipid Containing (CMFr) Fraction

Adult female cats weighing 2.4-3.2 kg. were anesthetized by an intramuscular injection of Ketamine at a preferred dosage of 7.0 mg/kg. Once anesthetized, a laparotomy was performed through a mid-line incision according to conventionally known surgical procedures. Omenta were surgically removed and placed into sterile plastic bags held a 4° C. for immediate processing. Simultaneously, subcutaneous fat was also removed and treated in a manner identical to the omental tissue for use in procedures as a non-omental lipid control. Using proper aseptic technique, the omenta were weighed, spread out onto a plastic surface and cut into individual pieces approximately four square centimeters in size using surgical scissors. These individual omental pieces, ranging in weight individually from 7 to 66 grams, were placed in a sterile Waring blender containing 300 ml of phosphate buffered saline (hereinafter "PBS") which was precooled to 4° C. The omental pieces were blended for five minutes at 20,500 rpm to yield an omental homogenate which was subsequently placed in sterile 250 ml plastic bottles and centrifuged at 1600 times gravity in a refrigerated centrifuge at 4° C. for twenty minutes. After centrifugation, three distinct and separable fractions were visible in the bottles: a pellet of mixed composition; a turbid homogenate containing substantially all the proteinaceous material, and a floating, cream colored, lipid cake. Each of these fractions was isolated individually.

The pellet of mixed composition was discarded completely. The turbid homogenate fraction was fully saturated (i.e. 100%) with aqueous ammonium sulfate which acted to precipitate the total protein in this fraction. Testing of the turbid homogenate fraction and the total protein precipitant (resuspended in PBS) by the cornea assay revealed that neither of these preparations had good angiogenic activity.

The lipid fraction isolated as a floating lipid cake was composed of two distinct layers: an upper foamy composition and a more dense, compact layer which was darker in color than the upper. Each layer was evaluated and found to contain an active angiogenic factor in substantial quantity. For this reason, each of these lipid layers individually and in combination comprise the active lipid fraction per se of the present invention. The weight of the lipid cake comprising both layers was found to be approximately 93% of the total weight of the omentum from which it was derived and it is this lipid cake which is used to prepare the concentrated organic extract comprising the active angiogenic factor composition.

Active lipid fractions were extracted using the quantities and proportions of lipid cake given in Table I below:

TABLE I

| Exp. No. | Total Omentum* | Lipid Cake* | Portion of Lipid Cake Extracted* |
|---|---|---|---|
| 1 | 31.2 | NR | 3.6 |
| 2 | 65.7 | 56.0 | 3.2 |
| 3 | 50.1 | 48.3 | 3.1 |
| 4 | 61.0 | NR | 7.1 |
| 5 | 38.0 | 37.0 | 3.5 |
| 6 | 39.9 | NR | 3.0 |
| 7 | 7.8 | 6.2 | 2.4 |
| 8 | 22.3 | 21.4 | 3.4 |

*Weight (gm)
NR = Not Reported

The indicated quantities of lipid cake were combined with approximately 21 ml of an organic solvent comprising chloroform and methanol (2:1, v/v) in an Eberbach 8575 microblender and homogenized for two minutes. The lipid/organic solvent homogenate was then centrifuged at 200 times gravity in a clinical centrifuge at room temperature for ten minutes to yield a clear, golden colored, supernatant and a particulate matter precipitate. The supernatant was isolated using conventional procedures and subjected to rotary evaporation at 37° C. under vacuum to completely remove the chloroform/methanol solvent. Other methods for solvent removal are known in the art and may be used in place of rotary evaporation. A viscous liquid was obtained which was then preferably suspended in approximately 4 ml of PBS for use in the cornea and cam assays.

II. Obtaining Purified Fractionates

The CMFr, obtained supra, was dissolved in a mixture of hexane (approx. 60 ml hexane for every 10 g of extract), and 0.66 volumes of 95% ethanol was then added. The phases were mixed thoroughly, and were allowed to separate. The upper phase (hexane), was re-extracted with 95% ethanol, and the resulting lower phase of the re-extraction was combined with the first ethanol fraction. The combined ethanol fractions were then re-extracted with hexane, and the resulting hexane layer combined with the first hexane fraction. Both phases were dried, to obtain "hexane upper phase material," and "ethanol lower phase material" (hexane-UP, and ethanol-LP, hereafter).

The ethanol-LP fraction was then subjected to Folch partition, following Folch, et al., J.Biol.Chem. 226:497–509 (1957) (i.e., the fraction was dissolved in chloroform/methanol (2:1, 20 volumes, v/wt), and 0.2 volumes of water were added. Phases were thoroughly mixed, and allowed to separate). The upper phase of the Folch partition was removed, and the lower partition was washed with 0.4 volumes methanol/water (1:1). This produces an upper methanol phase, which is combined with the Folch upper phase, and then dried to obtain the portion known hereafter as "Folch UP." The lower portion is also dried, and is known hereafter as "Folch LP".

The Folch LP portion was dissolved in chloroform, and was then subjected to chromatography on a silicic acid, Unisil column, as described by Vance, et al., J.Lipid Res. 8:621–630 (1967). The column was eluted successively with 20 column volumes of chloroform, acetone/methanol, (9:1), and methanol. This successive elution separates neutral lipids (chloroform), glycolipids (acetone/methanol), and phospholipids (methanol).

The Folch UP portion was dissolved in approximately 3 ml/mg of methanol/water (1:1), and was then applied to a C18 reversed-phase cartridge, as described by Williams, et al., J.Neurochem. 35(1): 266–269 (1980), and the cartridge was then washed with four volumes of methanol/water (1:1) to obtain "non-lipid UP material" after drying, and four volumes of chloroform/methanol (2:1), to obtain "lipid UP material" after drying.

Lipid UP material was then dissolved in methanol/chloroform/water (60:30:8), and was applied to a DEAE-Sephadex acetate column, following Christie, Lipid Analysis, Pergamom Press, 2nd edition, pp. 109–110 (1982). This column was then eluted with 10 volumes of the methanol/chloroform/water mixture used originally, to obtain what is referred to as "neutral lipid upper phase fraction," or "neutral lipid UP." Extraction with methanol/chloroform/0.8 sodium acetate (60:30:8) obtained ganglioside fractions. Both fractions were evaporated to dryness, and the glycoside fraction was desalted, using a C18 reversed phase cartridge.

The chloroform-methanol fraction was extracted with 1.0% acetic acid in a volume ratio of 1:10 (w/v) by stirring with a magnetic stirrer for 10–12 minutes. The extract was centrifuged at 2000 rpm for 5 minutes in 200 ml bottles. The top layer, i.e., the acetic acid-insoluble fraction was then removed. The acetic acid soluble fraction was combined with an equal volume of chloroform and was centrifuged as above to obtain a clean separation of the two phases. Each phase was backwashed twice with the opposite solvent and all chloroform phases were pooled. Evaporation of the chloroform yielded the "acetic acid soluble" fraction.

Affinity chromatography (heparin and gelatin binding) of the Folch UP and "PBS homogenate" fractions were performed as follows:

Heparin-Sepharose CL-6B beads or Gelatin-Sepharose beads (approximately 3 gm each) were washed with 450 ml water in a sintered glass filter. The sepharose beads were suspended in water and packed into a 2.5×9 cm chromatography column. Excess water was drained off and the dry sample (e.g., Folch-UP) was suspended in 0.01 phosphate buffer, pH 7.0 and applied to the column. Elution was performed with the same buffer (total 100 ml at a flow rate of 2 ml per minute). This was followed by a washing with 100 ml of water to remove salts from the column. Final elution of the heparin or gelatin binding material was performed with 50 ml of 0.5% acetic acid. After evaporation of acetic acid the material was resuspended in phosphate buffer for testing.

The chloroform/methanol (2:1 v/v) lipid fraction was further characterized as to its component parts or subfractions using silica gel or iatrobead liquid chromatography. For these chromatographic fractionations the procedures described in A. Kuksin, *Chromatography Part B*' (E. Heftmann, editor), Elsevier, New York, 1983, were used. In our method, 5.0 ml of the chloroform/methanol lipid extract was placed in a chromatography column containing silica gel (100-200 mesh Sigma Chemical Company) which was previously equilibrated with chloroform. Using the silica gel columns, elutions was performed in sequence using 100 ml aliquots of the following solvents: chloroform; ethyl acetate; ethyl acetate/methanol (3:1); methanol/water (4:1) followed by 200 ml of a solvent mixture comprising chloroform/methanol/acetic acid/water (25:15:4:2). Five individual elution fractions were obtained (I–V).

Gel permeation chromatography was performed on a Sephadex LH-20 column. One hundred mg of the chloroform-methanol extract, or of the ethanol-LP were placed on the column and elution was corned out with a chloroform-methanol (1:1) solvent. Fractions were collected and the solvent was evaporated for testing.

III. Analysis of the Fractions

The lower phase glycolipids were examined by HPTLC with chloroform/methanol/water (60:35:8) as the developing solvent and visualized with the orcinol spray reagent as described by Svennerholm, *J.Neurochem.* 1:42 (1956). They were also analyzed by HPLC as their perbenzoyl derivatives as previously reported by Ullman, et al., *J.Lipid Res.* 19:910-913 (1978). The upper phase complex neutral glycolipid fraction was examined by HPTLC and by immunoblotting with Forsmann and SSEA-1 antibodies. The major component of the upper phase complex neutral glycolipid fraction was further purified by preparative TLC or by chromatography on an Iatrobead column (1×50 cm, 60 u) eluted with hexane/isopropanol/water mixtures as taught by Kannagi, et al., *J.Biol.Chem.* 237(24) 14865-14874 (1982); and Hakomori, et al., *J.Biol.Chem.* 259(7) 4672-4680 (1984).

The ganglioside fraction was treated with 0.25N sodium hydroxide in methanol for 2 hrs at 37° C., neutralized with glacial acetic acid and desalted with a C18 reversed-phase cartridge. The alkali treated ganglioside fraction was then subjected to chromatography on a DEAE-Sephadex column and eluted with 0.02M, 0.08M and 0.05M ammonium acetate in methanol to obtain mono-, di-, and polysialo- ganglioside fractions, respectively. See Ledeen, et al., *Methods in Enzymol.* v.83, part D, pp. 139-191 (1982). The ganglioside fractions were separated into individual components by chromatography on a 0.4×50 cm, 10 μM particle, Iatrobead column eluted with chloroform/methanol/water (65:35:8). Fractions of 1.2 ml were collected, aliquots examined by HPTLC and fractions containing single components appropriately pooled. The non-lipid material was extracted with methanol, centrifuged and the supernatant removed. The insoluble residue was dissolved in water, and the water and methanol soluble fractions examined by HPTLC in several solvent systems.

Purified gangliosides were dried under nitrogen, and 300 μl of 0.05M sodium acetate buffer, pH 5.5, containing 0.025% $CaCl_2$ added. *V. cholerae* neuramindase (100 μl, 0.1 units) was added and the sample incubated for 3 hrs at 37° C. The reaction was stopped by the addition of 2 ml chloroform/methanol (2:1) and the mixture was placed over a reversed phase cartridge and the non-lipid components eluted with water. Any remaining gangliosides and lipid reaction products were eluted with methanol and chloroform/methanol and examined by HPTLC. The liberated sialic acids were also examined by TLC as their trimethylsilyl derivatives following Ledeen, supra.

For sugar and fatty acid analysis, the glycolipids were subjected to methanolysis in anhydrous 0.75N HCl in methanol following Ledeen, supra, and Kozulec, et al., *Analytical Biochem* 94:36-39 (1979). The fatty acid methyl esters were analyzed by TLC. The methyl glycosides were analyzed as their trimethylsilyl derivatives on the same OV-1 column as described by Kozulec, supra. For HPLC analysis of the lower phase neutral glycolipids, the fraction was perbenzoylated with benzoyl chloride in pyridine and the benzoylated glycosphingolipids separated and quantitated by HPLC on an uncoated Zipax column with gradient elution and 230 nm detection as previously described by Ullman, supra. For direct probe mass spectrometry, glycolipid or ganglioside samples (5-50 ug) were trimethylsilylated in 25 ul of pyridine/hexamethyldisilane/trimethylchlorosilane/N,O-bistrimethylsilyltrifluoro acetamide. Anywhere from 1 to 5 ug of the derivative was placed in a sample cup and the probe was heated from 100° to 350° C. at a rate of 30°/min. The mass spectra were obtained with a Finnigan model 4500 quadrupole mass spectrometer equipped with Teknivent, model 56K data system. It was operated with an ionizing current of 0.5 ma and an ionizing voltage of 70 eV. The ionizer temperature was 150° C. Repetitive scans of the mass range from 100 m/e to 950 m/e were acquired at 5 sec intervals.

Glycolipids were chromatographed on aluminum-backed HPTLC plates with chloroform-methanol-water (60:35:8), dried, then dipped in 0.05% polyisobutyl methacrylate in hexane as described by Brockhause et al, *J.Biol.Chem.* 256:13223-13225 (1981). The plates were then soaked in phosphate buffered saline containing 1% bovine serum albumin for 2 hours before similar exposure to antibody for 2 hours at 40° C. The plate of upper phase neutral glycolipid was treated with Forssman monoclonal antibody IgM, purchased from American Type Culture Collection (T1B 121). The TLC plates of the disialoganglioside fraction was treated with GD3 monoclonal antibody IgM prepared by the inventors. After washing in PBS the plates were exposed to goat anti-mouse IgM conjugated to horseradish peroxidase for 2 hours at 4° C. After washing in PBS, the plates were developed with 33 mN 4-chloronaphthol in 0.02M Tris-HCl buffer containing 20% methanol and 0.025% $H_2O_2$.

IV. Characteristics of the Fractions

Figure 2:
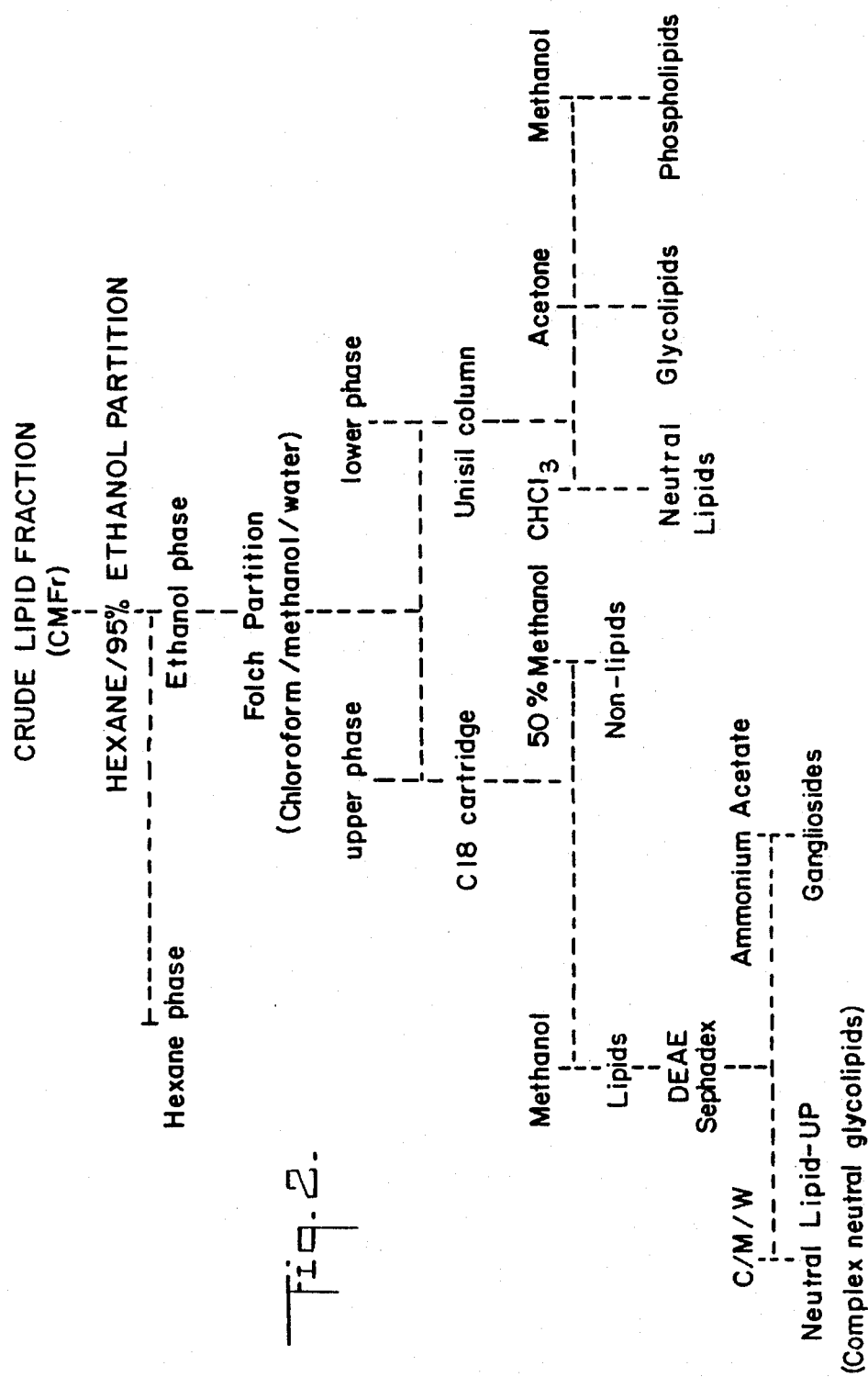
FIGS. 2 and 3 show methods for further fractionating the CMFr fraction obtained by the method of FIG. 1.

Feline omentum was homogenized, centrifuged and the floating lipid cake was extracted with chloroform/methanol and further fractionated as shown in FIG. 2. The hexane phase contained approximately 98% of the material in the CMFr and was shown to consist primarily of triglycerides, as determined by TLC. Alkaline methanolysis and GC/MS analysis of the resulting fatty acid methyl esters revealed that 14:0, 16:0, 16:1, 17:0, 18:0, 18:1 and 18:2 were the major triglyceride fatty acids (i.e., the first number indicates the carbon chain length of the fatty acid, the second the number of unsaturated bonds).

The ethanol phase material was subjected to Folch solvent partition and the lower phase lipids, which constituted 80% of the ethanol phase lipids, were fractionated on a Unisil column. The neural lipid fraction recovered from the Unisil column also consisted primarily of triglycerides and small amounts of cholesterol and free fatty acids were detected by TLC analysis. The acetone glycolipid fraction was examined by TLC and components migrating as hexosylceramide, lactosylceramide, globotriaosylceramide and globoside were present. Quantitative analysis of these glucolipids by HPTLC is described infra. The methanol phospholipid fraction was examined by TLC and components migrating as phosphatidylserine, phosphatidylcholine and sphingomyelin were present.

Approximately 20% by weight of the ethanol-phase material was recovered in the Folch-UP. This Folch-UP material was applied to a reversed-phase cartridge and the non-lipid fraction eluted with methanol-water and the lipids eluted with chloroform/methanol. The lipid-UP material, was applied to a DEAE column and the neutral lipid fraction, which was not retained by the column, was collected and found to constitute 40% of the lipid-UP material. Upon examination by HPTLC this fraction was found to contain primarily a glycolipid migrating below globoside, and small amounts of more complex glycolipids.

The ganglioside fraction was eluted from the DEAE column with ammonium acetate in methanol and desalted with the use of a reversed phase cartridge. Examination by HPTLC revealed the presence of resorcinol components migrating as GM3, GM1, GD3 and several minor polysialoganglioside components. The further purification and identification of these gangliosides is described inra.

The non-lipid upper phase fraction (non-lipid-UP) was taken to dryness and extracted with methanol. The majority of material was not methanol soluble and the suspension was centrifuged and the supernatant removed. The insoluble material was readily soluble in water. These fractions were examined by TLC and the water soluble fraction showed only one ninhydrin positive band. The bulk of this water soluble material appeared to be salt. The methanol soluble material contained at least six orcinol and ninhydrin positive components and a GC/MS analysis, after trimethylsilylation, indicated this material was a complex mixture of sugars, amino acids, peptides and glycopeptides. Weight distribution of the fractions from the omentum crude lipid extract is shown in Table II.

Figure 3:
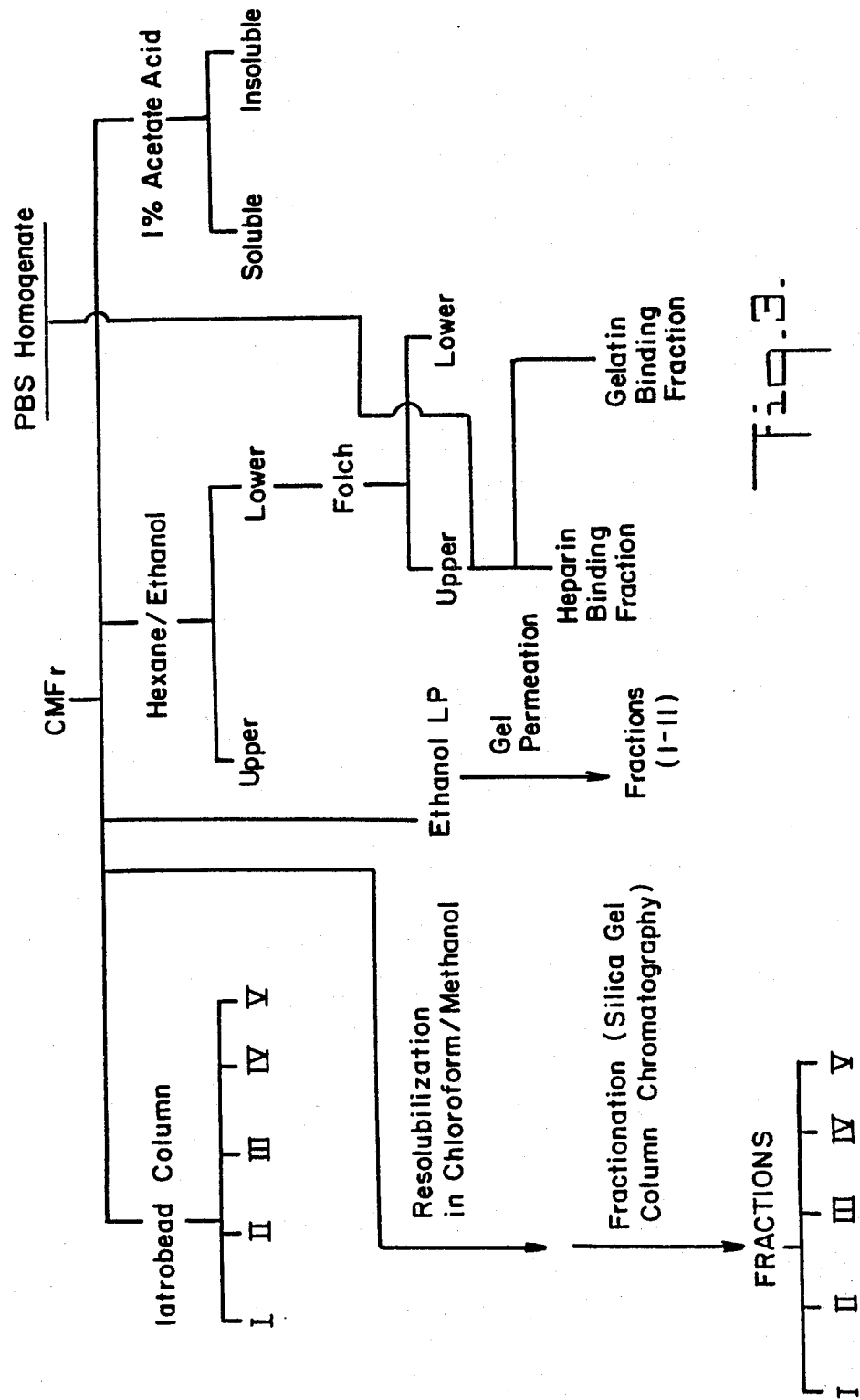

Aliquots of the glycolipid fraction were benzoylated with benzoyl cloride in pryidine and the perbenzoylated derivatives analyzed by HPLC with 230 nm detection. The results are shown in FIG. 3. These data show that the percent distribution of glycolipids in this fraction as GlcCer (Nfa), 26%; GalCer (Nfa), 9.6%; GlcCer (Hfa) +GalCer (Hfa) +GaOse2Cer (Nfa), 12%; LacCer, 11%; GbOse3Cer, 10%; GbOse4Cer, 26%.

The upper phase neutral lipid fraction was examined by HPTLC and found to consist of about 90% of an orcinol positive material migrating slightly more slowly than the globoside standard, as well as small amounts of 3 to 4 more polar orcinol positive components. Immunoblotting with Forsmann and SSEA-1 antibody indicated the major component was Forsmann positive and no SSEA-1 positive components were present. The major component was further purified by chromatography on an Iatrobead column and subjected to methanolysis and component analysis by GC/MS.. Hexose ratios were found to be Glc/Gal/NAcGal 1:2:2. The intact glycolipid was also silylated and examined by direct probe mass spectrometry. The spectra, show in FIG. 3, indicated the presence of terminal hexosamine, internal hexose residues, the presence of C-18 sphingosine and fatty acids. Taken together these data indicate that the glycolipid is the Forsmann pentaglycosylceramide. Although position and configuration of linkages have not been directly determined, the antibody reactivity and glycolipid analytical data strongly support this structure.

The ganglioside fraction was treated with mild alkali to destroy any ester linkages that may have been present and separated into mono, di and polysialoganglioside fractions by DEAE-Sephadex chromatography. The monosialoganglioside fraction was shown by HPTLC to consist primarily of components migrating as a triplet of bands corresponding to the mobility of the GM3 standard and a small amount of material migrating as GM1. The monosialoganglioside fraction was further purified by chromatography on an Iatrobead column and the fractions containing only components migrating as GM3 were pooled. This material was treated with neuraminidase and the lipid product was characterized as lactosylceramide by HPTLC and direct probe-MS. The liberated sialic acid was shown by GC analysis to consist only of N-acetylneuraminic acid. The intact ganglioside was subjected to methanolysis and the sugars and fatty acids examined by GC analysis. The ratio of Glc/Gal was found to be 1:1 and the fatty acids consisted of primarily of 16:0, 18:0, 18:1, 20:0, 22:0, 23:0, 24:0 and 24:1. The preparation was also examined by direct probe mass spectrometry as the trimethylsilyl ether derivative. A mass spectra similar to that given by ganglioside GM3 standard (sialyl [2-3]galalctosyl[1-4]glucosy [1-1] ceramide).

The disialoganglioside fraction was shown by HPTLC to consist primarily of a component migrating as GD3. This material was further purified by chromatography on an Iatrobead column and the fractions containing only a single component migrating as GD3 were pooled. The preparation was subjected to methanolysis and the methyl glycosides and fatty acid methyl esters examined by GC/MS. The ratio of Glc/Gal was found to be 1:1 and the major fatty acid components were 16:0, 18:0, 18:1. 24:0, 24:1. The material was treated with neuraminidase and the lipid product identified as lactosylceramide by HPTLC and direct probe MS analysis. The liberated sialic acid was shown to consist only of N-Acetylneuraminic by GC analysis. Direct probe MS of the TMS derivative gave spectra consistent with GD3. The material was also shown by immunoblotting to react with a monoclonal antibody prepared in this laboratory with demonstrated reactivity with GD3.

The polysialoganglioside fraction was shown to contain components migrating on HPTLC as ganglioside GD1a, GT1b, but insufficient quantities were obtained for further analysis.

V. Angiogenesis

The angiogenic activity of the lipid preparations described in Figure I and of the Silica Gel chromatography fractions I-V were tested by the rabbit cornea test in the following manner: a series of New Zealand white rabbits were anesthetized with intravenous pentobarbitol (30 mg./Kg). From each preparation shown in Table I, a single 50 microliter injection of the aqueous lipid suspension was made through a 25 gauge needle placed intrastromally into the cornea of each eye. The corneas of the animals were examined grossly and with an operating microscope on the second, fourth, sixth, eighth, and tenth day following ocular injection. Blood vessel growth and the presence of any corneal edema and/or inflammation was noted. On the tenth day after examination visually, the rabbits were individually sacrificed and histological slides, stained with hematoxylin and eosin in the conventional manner, were obtained from six micrometer thick sections cut from the formalin fixed enucleated eyes. Photo records of positive rabbit eyes were recorded.

The angiogenic response was graded as follows: 0, identified no angiogenesis and a clear cornea; 1+, identified dilation of scleral vessels with red coloration noted at the limbus; 2+, identified several individual blood vessels migrating from the limbus two thirds of the way to the injection site; 3+, identified multiple blood vessels extending from the limbus to the injection site involving 10-20% of the cornea; 4+, identifies dense blood vessel formation extending from the limbus to the injection site involving at least 30-40% of the cornea.

For comparison purposes, an aqueous suspension of the omental lipid cake and an aqueous preparation of the subcutaneous non-omental fat were also prepared and tested. The non-omental fat preparation was made by combining a three gram portion of the fatty subcutaneous tissue with 4 ml of PBS and homogenizing this mixture using the Eberbach microblender for two minutes at 4° C. Similarly, an aqueous suspension of the omental lipid cake was prepared by homogenizing four gram portions of the lipid cake with 4 ml of PBS in the microblender for two minutes at 4° C. The homogenate of the whole omentum prior to centrifugation into proteinaceous fractions and lipid fractions was also evaluated. The results are as shown in Table II below.

TABLE II

| | Test Sample | | Angiogenic Activity (per 50 microliter) |
|---|---|---|---|
| 3 | Extracted | | |
| 4 | lipid preparation | | |
| 5 | in aqueous | | |
| 6 | medium - | No. 1 | 4+ |
| 7 | | No. 2 | 4+ |
| 8 | | No. 3 | 3+ |
| 9 | | No. 4 | 4+ |
| 10 | | No. 5 | 3+ |
| 11 | | No. 6 | 4+ |
| 12 | | No. 7 | 4+ |
| 13 | | No. 8 | 4+ |
| 14 | PBS homogenate | | |
| 15 | of lipid cake | No. 1 | +1 |
| 16 | | No. 2 | +1 |
| 17 | | No. 3 | +1 |
| 18 | PBS homogenate | | |
| 19 | of whole omentum | No. 1 | +1 |
| 20 | | No. 2 | +1 |
| 21 | | No. 3 | +1 |
| 22 | PBS homogenate | | |
| 23 | of non-omental | | |

TABLE II-continued

| | Test Sample | | Angiogenic Activity (per 50 microliter) |
|---|---|---|---|
| 24 | fatty tissue | No. 1 | 0 (inflammation) |
| 25 | | No. 2 | 0 (inflammation) |
| 26 | | No. 3 | 0 (inflammation) |
| 27 | PBS alone | No. 1 | 0 |
| 28 | | No. 2 | 0 |
| 29 | " | No. 3 | 0 |

The data indicates that excellent angiogenic activity was observed after a single 50 microliter central corneal injection of the chloroform/methanol lipid extract. In comparison, only minimal angiogenic activity was noted with the PBS homogenate of the total omentum and with the PBS homogenate of the total omentum and with the PBS homogenate of the lipid cake prior to extraction. Note, however, that a heparin binding component was concentrated by affinity chromatography from the PBS homogenate which showed good angiogenic activity with the CAM assay (see page 38). No angiogenesis at all occurred in those instances following injection of PBS alone or the subcutaneous non-omental fat PBS homogenate. A complication however, noted in the data of Table II, was that the injected subcutaneous fat taken from the cat abdominal wall caused severe inflammation of the cornea within two days after corneal injection.

Figure 4:
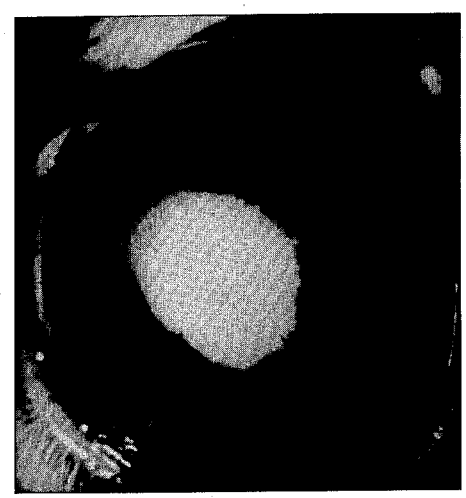
FIG. 4 illustrates capillary formation in rabbit cornea after treatment with CMFr.
Figure 5:
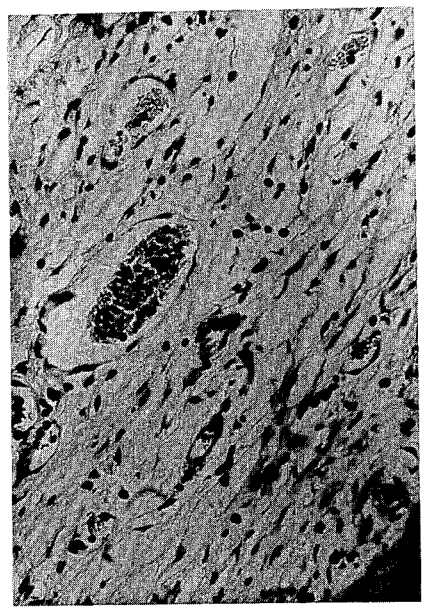
FIG. 5 shows multiple capillary formation in the stroma.
Figure 6:
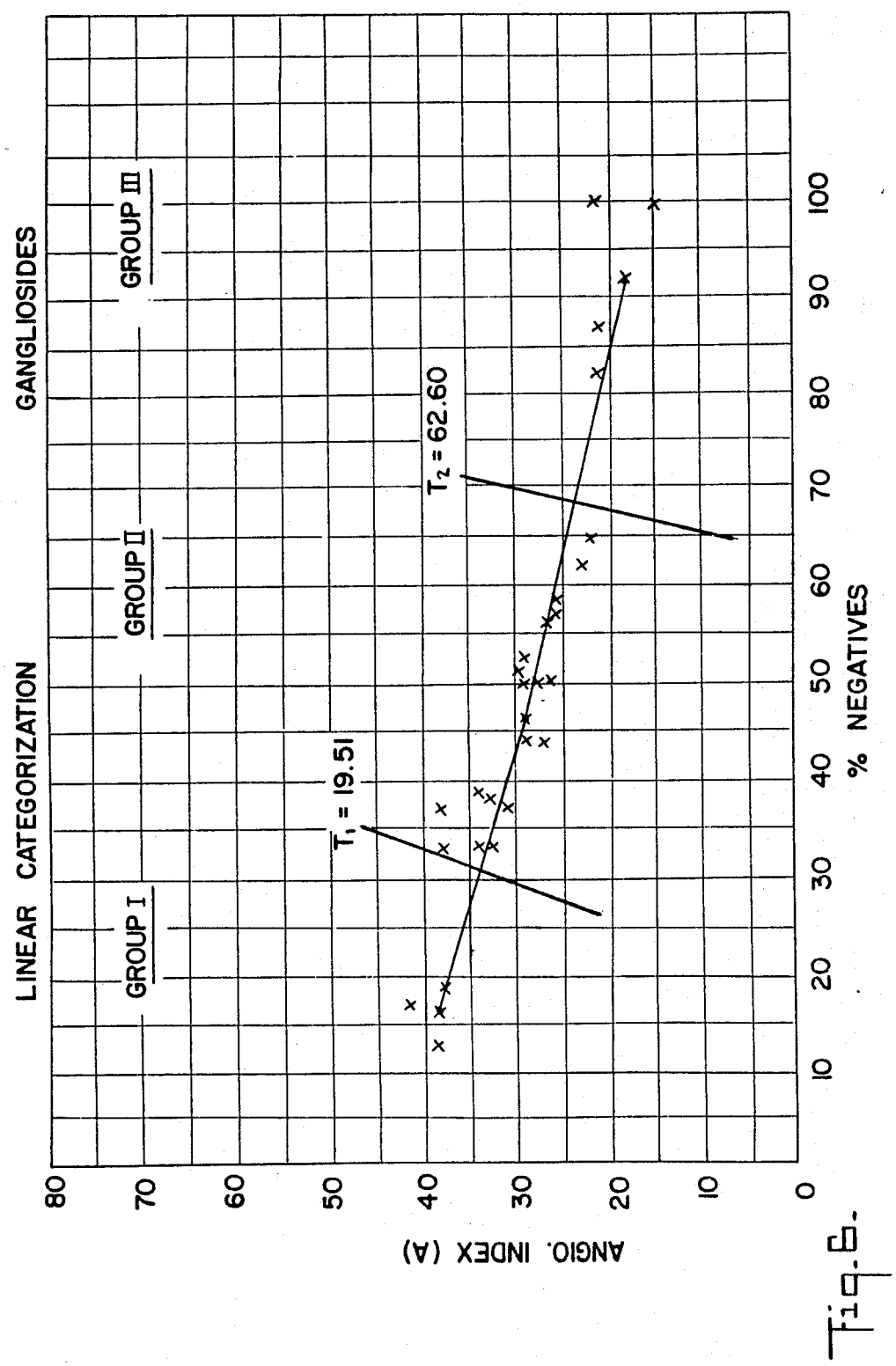
Figure 9:
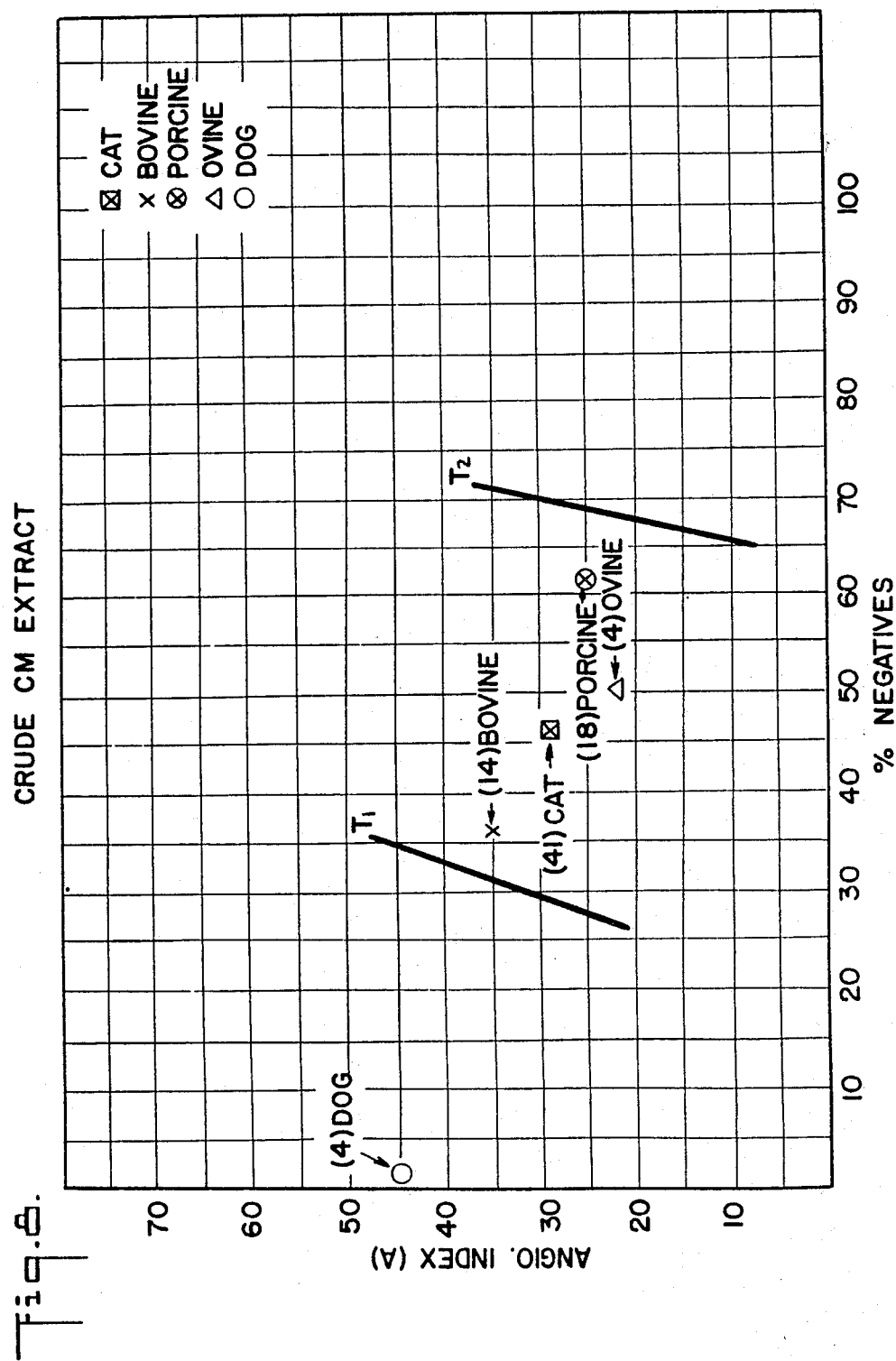
Figure 9:
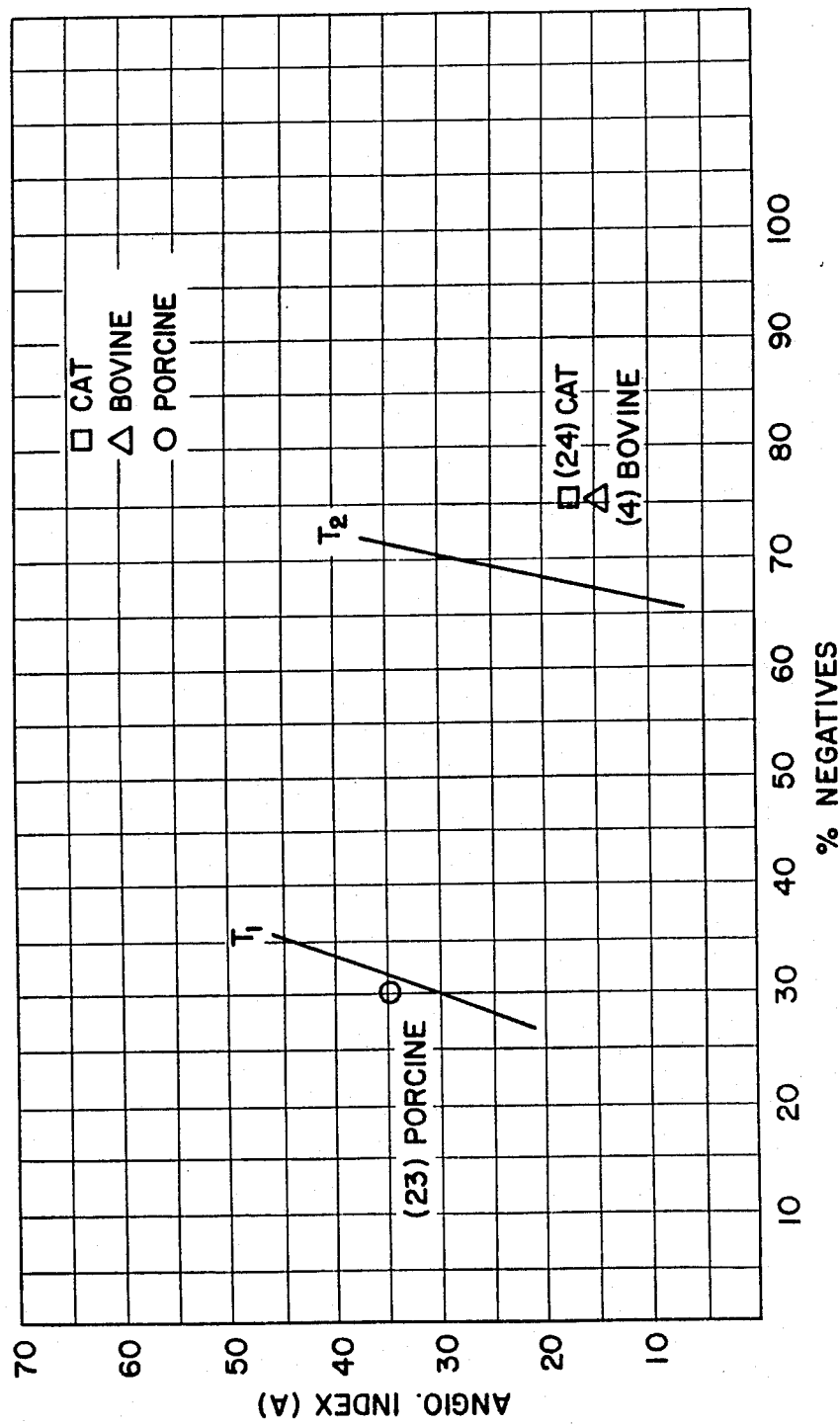
Figure 10:
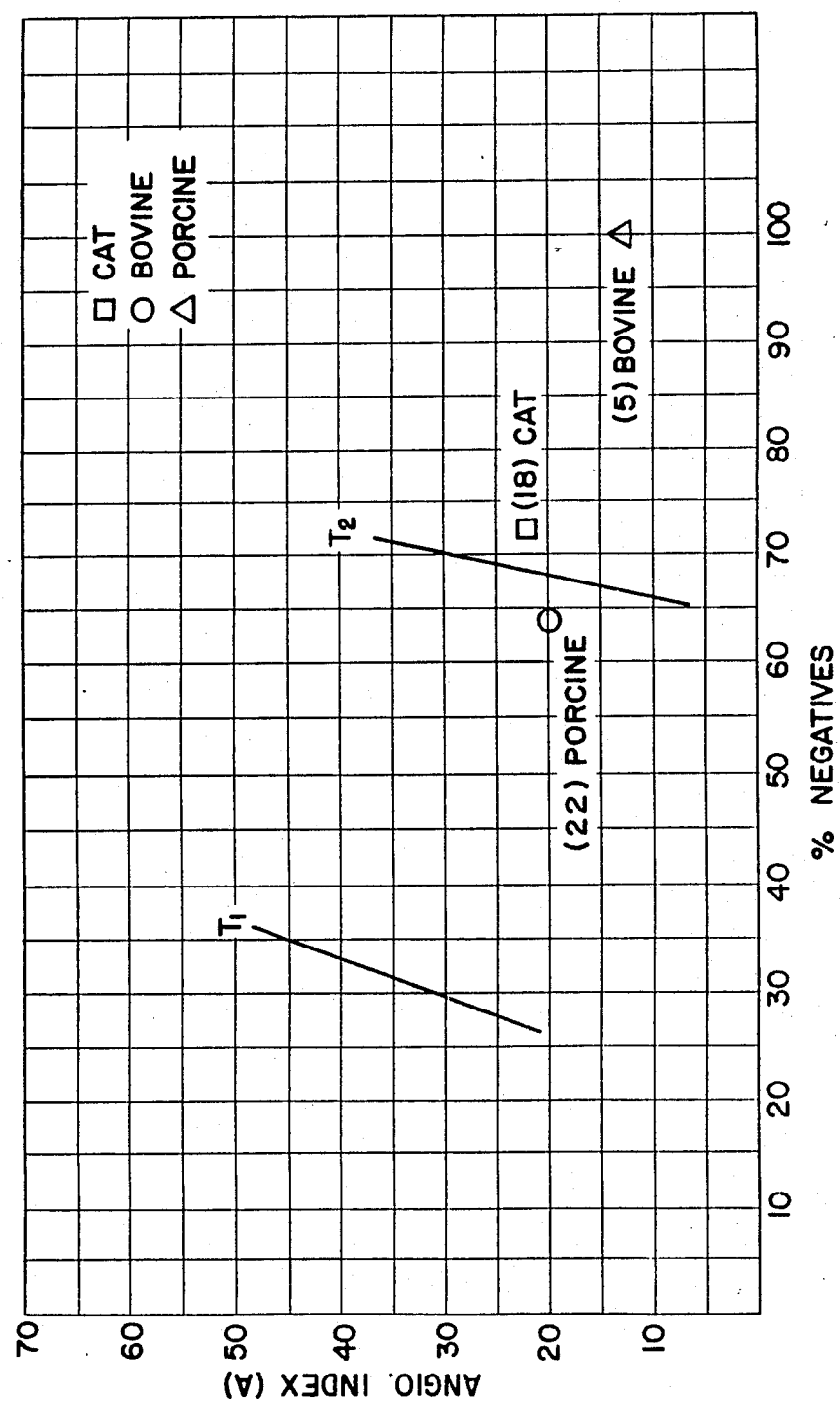
Figure 11:
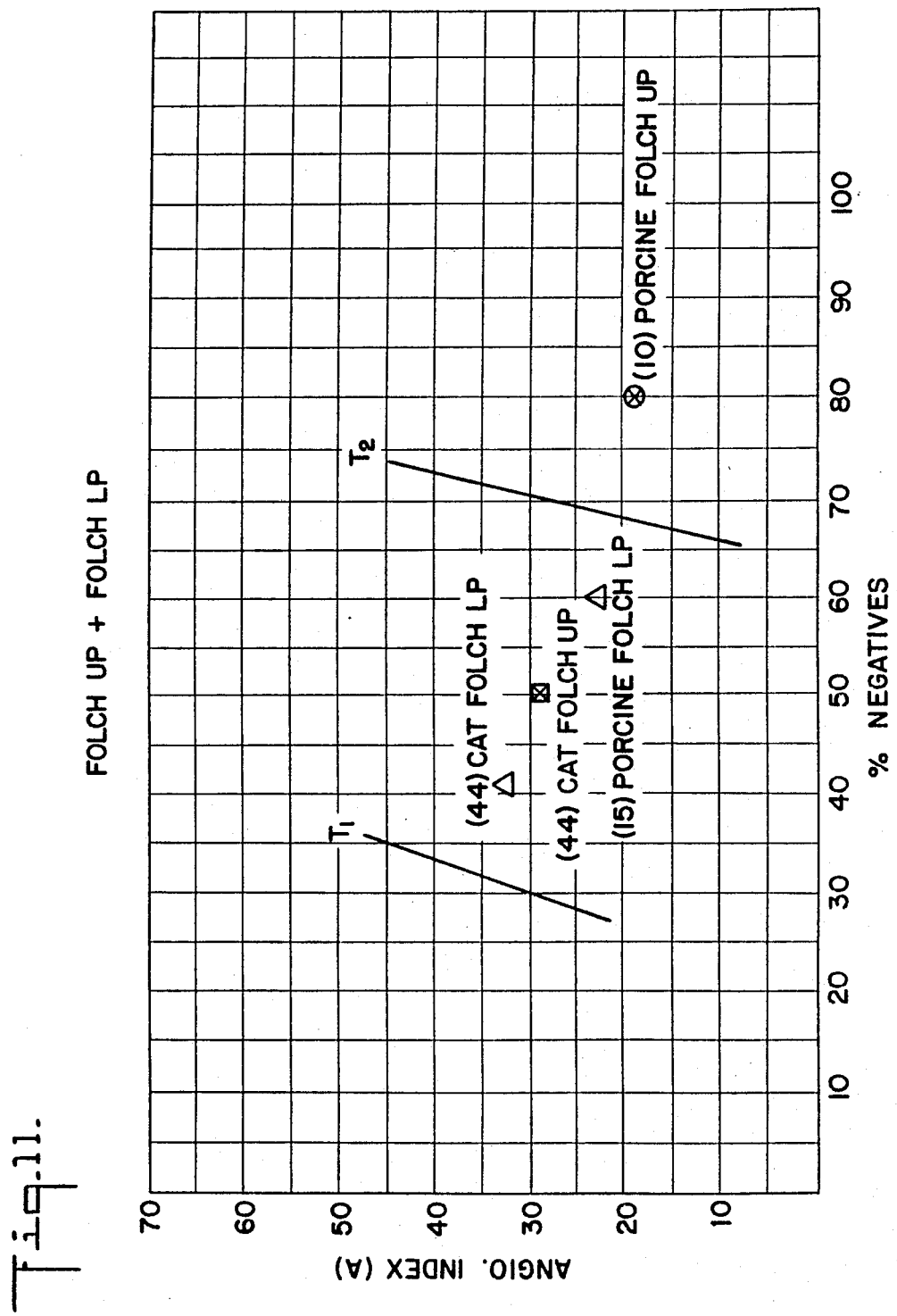
Figure 12:
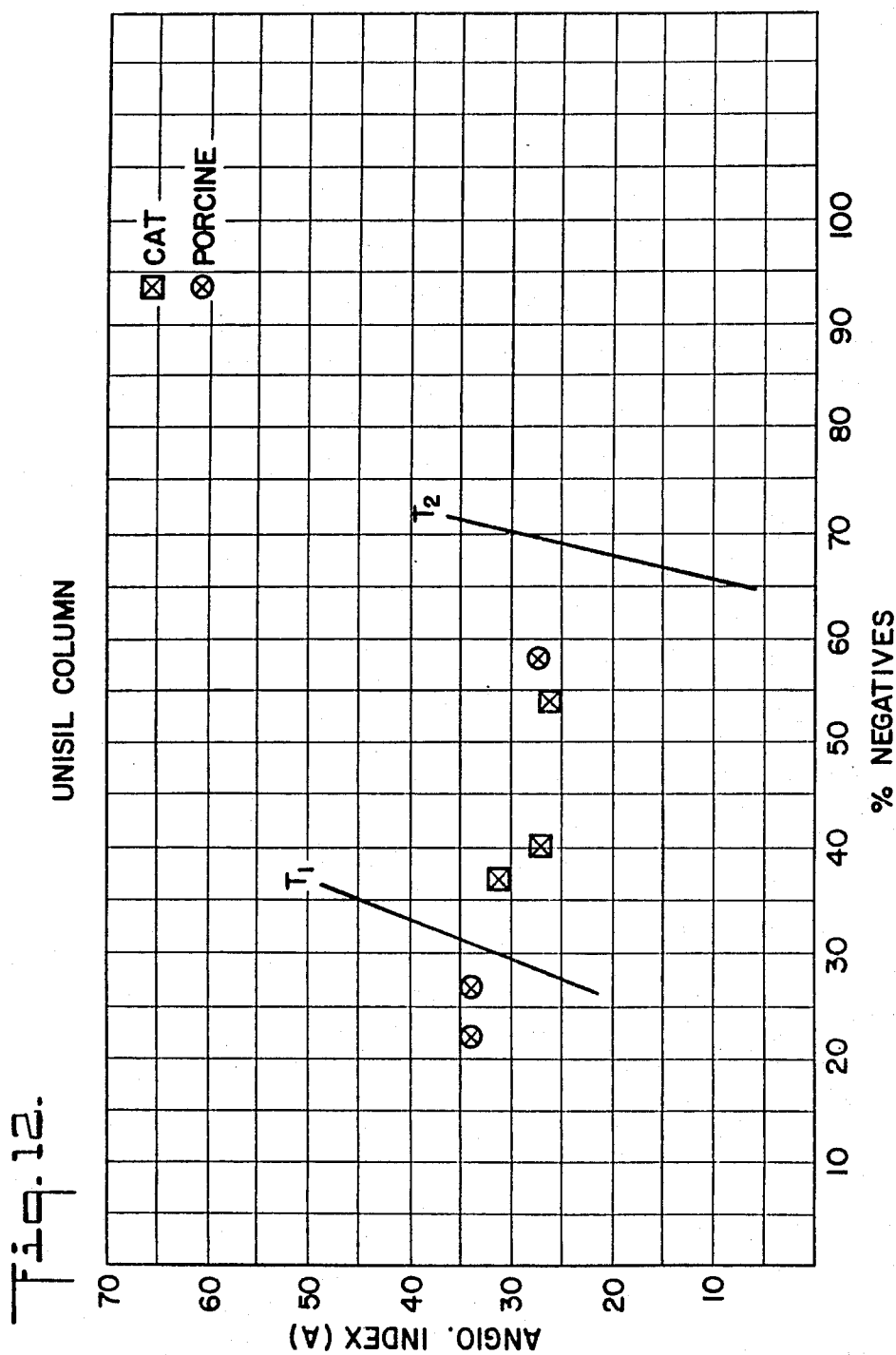
Figure 13:
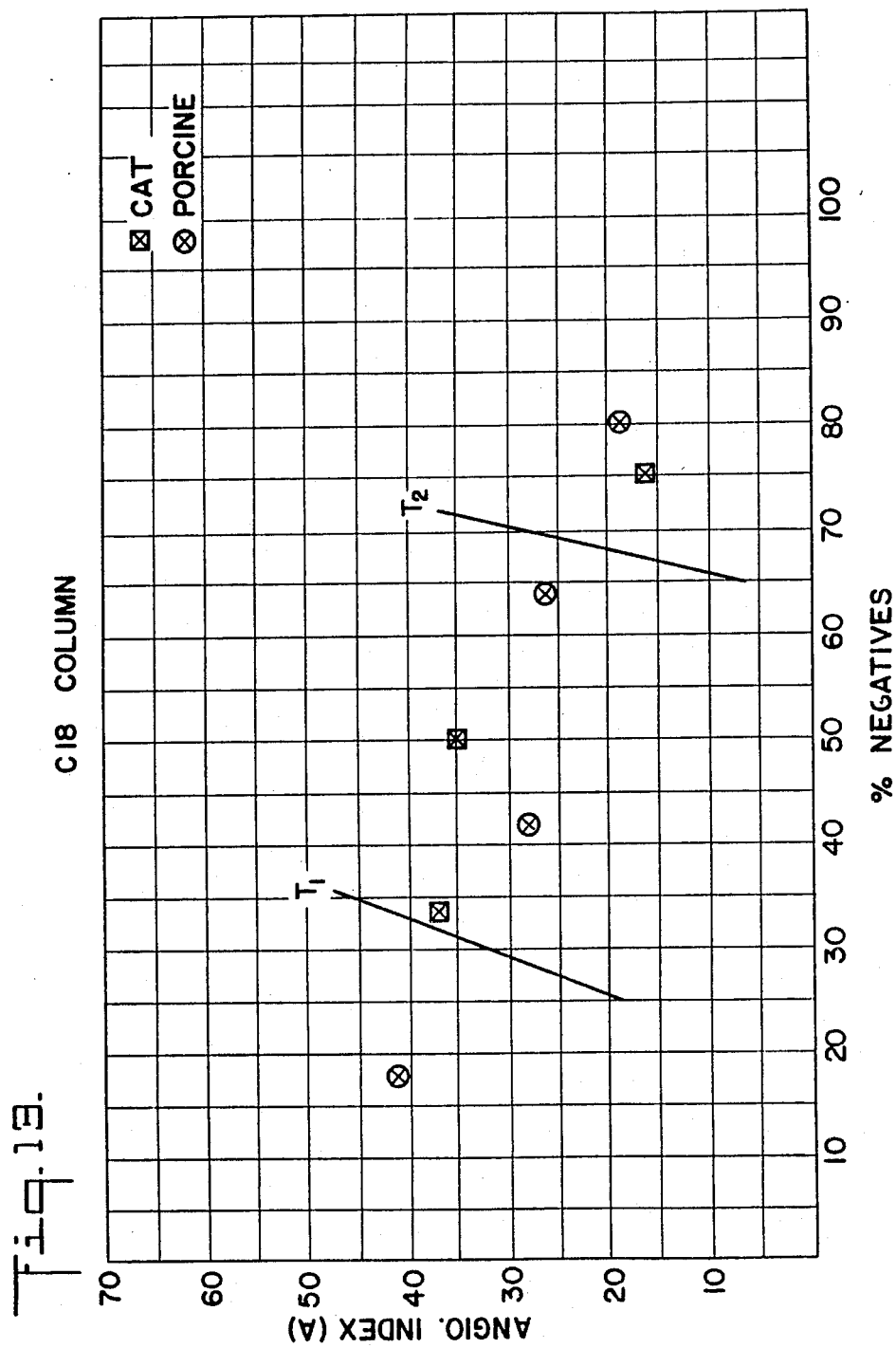
Figure 14:
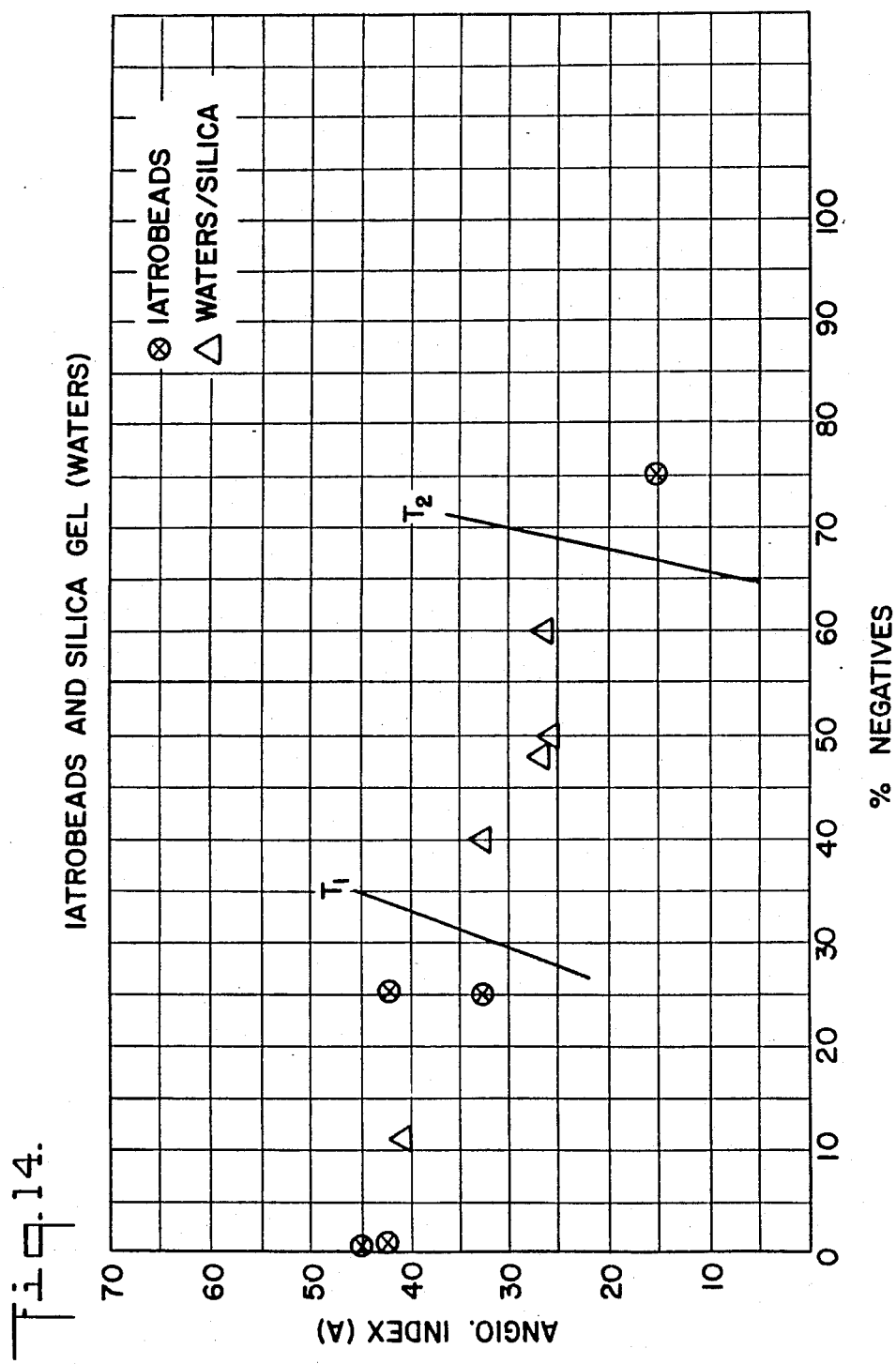
Figure 15:
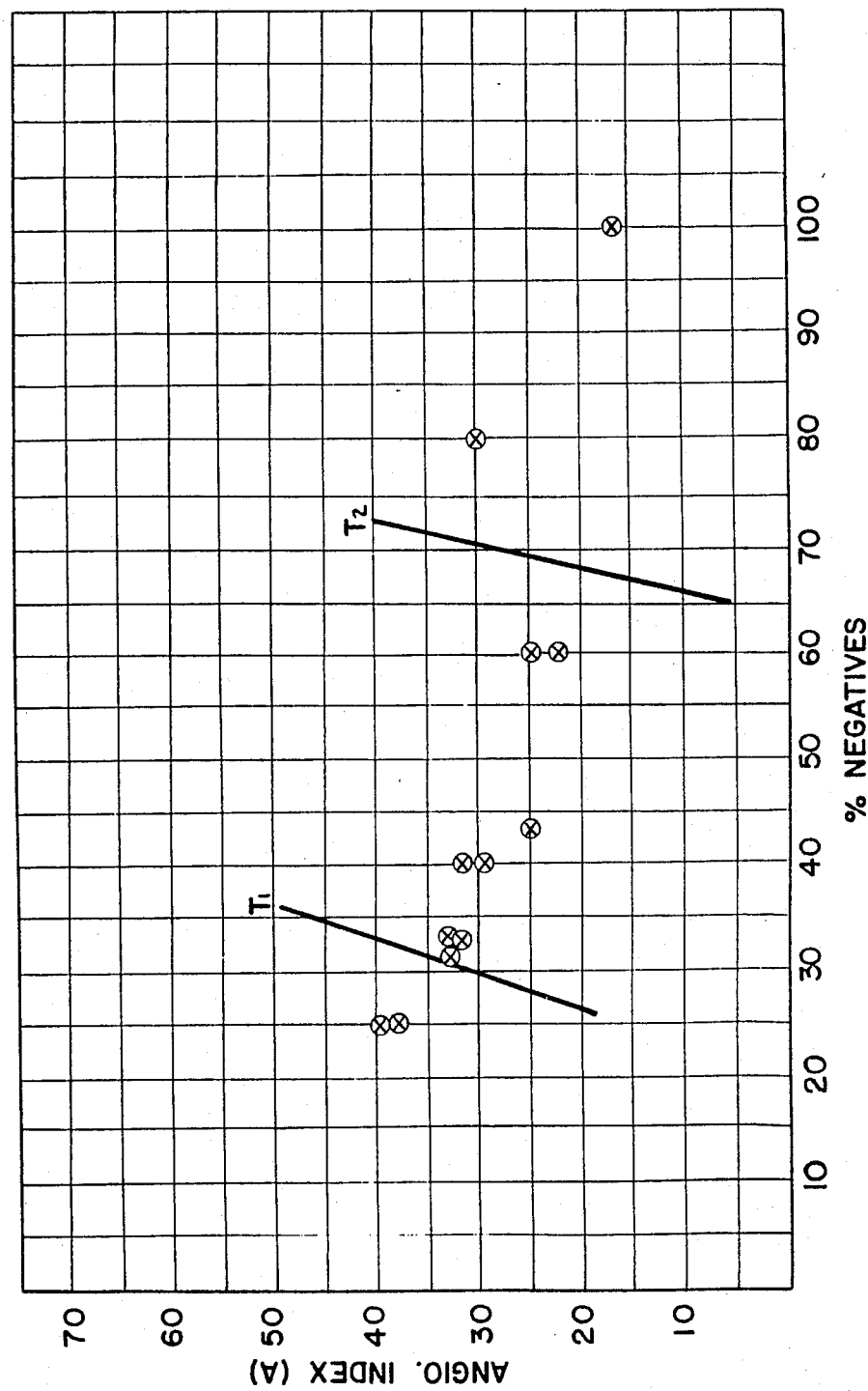

The course of the angiogenic response in the cornea to the injected aqueous suspended chloroform/methanol lipid preparation followed a consistent pattern of rapid development and intense activity. Following injection of the extracted lipid fraction, a mild corneal inflammatory reaction was observed within twenty-four hours which subsided within forty-eight hours. This initial inflammation is characterized by slight clouding of the cornea with minimal erythema in the scleral area which was often accompanied with a slight discharge from the eye. A pannus, the appearance of a curtain of blood vessels around the margin of the cornea, with interstitial blood vessel formation became grossly evident 3 to 4 days following the injection. By the seventh to tenth day, the blood vessels had formed a dense and richly structured network within the cornea. This is illustrated by the photograph in FIG. 3. Histological examination of the enucleated eyes harvested on the tenth day showed multiple capillaries within the corneal stroma; a photograph of the histological section illustrating such multiple capillaries within the stroma is shown in FIG. 4.

It is of particular note that the solvent extracted lipid fraction in aqueous medium initiates and sustains angiogenesis after only a single 50μl dose injection. Although the mechanism of this angiogenic process and response is presently unknown, it is apparent that the injection of the extracted lipid fraction from the omentum initiates and develops new blood vessel formation which becomes organized into dense, well structured, vascular networks in seven to ten days.

As shown in FIG. 3 further fractionation of the CMFr was performed by silica gel chromatography. Subsequent testing of each of the five lipid subfractions, with the cornea assay showed angiogenic activity to be present only in subfraction V with ano noticeable angiogenic effect from any of the subfractions I-IV. The overall activity of subfraction V however, was measurably less than the chloroform/methanol lipid extraction preparation originally obtained. It was subsequently found that subfactors I-IV, although having no angiogenic activity in and of themselves, when combined with subfraction V act to enhance and increase the activity and potency of the angiogenic composition as a whole.

The experiments set forth supra show that the CMFr exhibits angiogenic activity. Further experiments were then performed, using additional fractions prepared following the outline of Figure I. The experiments consisted of performing CAM assays, described infra. This leads to the derivation of the "Angiogenic Index", which is a measure of the effect the fractions had in the CAM assays. An additional value, the "Discrimination Unit", is also derived. Both of these are explained infra.

The experiments described were not confined to the omental fractions obtained by the experiments described supra. Once the general molecular composition of the more effective fractions was determined to contain lipidcontaining molecules, especially gangliosides, additional lipid-containing molecules which are known to the art, were used. It was unexpectedly found that many of these materials also possessed strong, unexpected angiogenic activity. Additionally, experiments were performed using commercially available gangliosides, in new combinations. Again, unexpected angiogenic properties were found. Of even greater interest is the fact that compositions with mixtures of different gangliosides had greater than additive angiogenic effect.

VI. CAM Assays

Angiogenic properties of extracts, fractionates, and compositions were determined by subjecting these to Chick Embryo Chorioallantoic Membrane Assays ("CAM assays").

The CAM assay uses fertile chicken eggs, and involves the following steps:

Preparing the Eggs: By using a power drill, a 2 cm square of shell is removed from the fertilized egg on day 4 of incubation. The opening is now referred to as a "window". Cellophane tape tightly seals off the window to the outside environment. The eggs are then put in the 37° C. incubator for another 4 days.

Making the Discs: On the 8th day after incubation, 0.4 g of agarose and 10 ml of PBS are mixed and heated to 100° C. in a small glass vial and subsequently mixed at 50° C. with a 2% BSA solution (in PBS). The mixture (2% agarose plus 1% BSA in PBS) is kept warm in a water bath. Using a pipet 20 to 40 ml of the testing solution (i.e., extract, fractionate, or composition) is mixed with a drop of the agarose mixture by constant stirring. After the large disc is hardened by gelation, it is subdivided into 4 smaller discs.

Placing the Discs on the Membrane: On the 8th day after incubation, the discs are placed inside the eggs on the CAM; choosing areas on the CAM with various degrees of blood vessel development. The selected area is approximately 1 cm away from the chick embryo but not so far away that the disc will lie beyond the CAM or stick to the inside shell wall. The eggs are then incubated for another 4 days. All instruments used are previously soaked in 98% ethanol.

Plastic Discs: Plastic discs were prepared using a hole puncher. After placing 2.5 ml of the test solution on each disc, the solution is allowed to dry over a warm plate. Additional 2.5 ml aliquots of the test solution may be added to the disc and dried between applications.

After the disc is prepared, it is placed on the CAM as described supra.

Rating the Effects: Upon the 12th day of incubation, the discs are located inside the eggs and the windows are made larger by breaking off bits of the shell with a pair of forceps.

The eggs are then examined under the light microscope. The vascularization in the rest of the egg is compared to that surrounding the disc. Degrees of neovascularization in the direction of the disc is determined and compared with the effects of the discs in other eggs. The effects of each disc is rated on a scale of 1 to 5, as follows:

1 = one or two small areas of increased branching around the disc; essentially negative.

2 = three or more small areas of increased branching around the disc; a weak response.

3 = formation of "wheel spoke effect," which is self explanatory; increased branching around the disc; a moderate response.

4 = "wheel spoke effect" with increased branching around the disc, to a degree greater than in "3"; a strong response.

5 = "wheel spoke effect" with extensive branching around the disc; a very strong response.

Plus and minuses are also used, with each numerical value, so a CAM assay could have a value ranging from 1- (no response whatsoever) to 5 (exceptionally strong response, with extensive branching).

Based upon the foregoing scoring system, the ANGIOGENIC INDEX (A"Index" or "A" in the following tables) is determined. The A Index allows for comparative analysis of samples, in terms of angiogenic activity. The Angiogenic Index is defined as:

$$100 \times \frac{\text{Total of scores on individual assays}}{\text{Maximum score possible.}}$$

For example, in a sample containing 12 CAM assays, if 7 are "weak," 1 is "moderate," none are "strong," and 4 are "negative" the A Index would be calculated as follows:

$$A = \frac{7(2) + 1(3)}{12 \times 5} \times 100 = 28.33$$

Table III sets forth data obtained by analyzing extracts, and solvent partition components obtained using the procedures set forth in FIGS. I, II and III. The terminology used is the same as that used in the Figures.

The samples were obtained from feline, bovine, porcine, and canine omenta, as indicated.

TABLE III

| COMPOUND | EXTRACTION | | | | |
| --- | --- | --- | --- | --- | --- |
| | EGGS | A | % NEG | W | M | S |
| Cat CMFr | 41 | 28.98 | 46.34 | 17 | 4 | 1 |
| Bovine CMFr | 14 | 35.27 | 35.71 | 5 | 4 | 0 |
| Porcine CMFr | 18 | 24.9 | 61 | 7 | 0 | 0 |
| Ovine CMFr | 4 | 23.35 | 50.00 | 2 | 0 | 0 |
| Canine CMFr | 4 | 45.05 | 0 | 3 | 1 | 0 |
| CatPBS supernatant | 15 | 19.12 | 73.33 | 4 | 0 | 0 |
| 1% HAc sol, UP | 18 | 28.17 | 44.44 | 6 | 4 | 0 |
| 1% HAc insol, LP | 10 | 28.72 | 70.00 | 1 | 2 | 0 |
| Cat subcut. fat | 6 | 20.03 | 83.33 | 0 | 1 | 0 |
| Porcine subcut. fat | 8 | 33.43 | 37.50 | 5 | 0 | 0 |
| Cat lipid cake | 5 | 13.36 | 100 | 0 | 0 | 0 |
| CMFr supernatant (cat) | 16 | 34.7 | 38 | 9 | 1 | 0 |
| CMFr pellet (cat) | 19 | 39.0 | 32 | 9 | 4 | 0 |
| CMFr supernatant | | | | | | |

TABLE III-continued

| | | | | | | |
|---|---|---|---|---|---|---|
| (porcine) | 7 | 32.4 | 43 | 4 | 0 | 0 |
| CMFr pellet (porcine) | 8 | 40.1 | 25 | 5 | 1 | 0 |
| SOLVENT PARTITION | | | | | | |
| Cat-Hexane UP | 24 | 16.7 | 75 | 6 | 0 | 0 |
| Bovine-Hexane UP | 4 | 15.05 | 75 | 3 | 1 | 0 |
| Porcine-Hexane UP | 23 | 35.4 | 30 | 16 | 0 | 0 |
| Cat-Ethanol LP | 18 | 21.9 | 72 | 5 | 0 | 0 |
| Bovine-Ethanol LP | 5 | 13.36 | 100 | 0 | 0 | 0 |
| Porcine Ethanol LP | 22 | 19.4 | 64 | 7 | 1 | 0 |
| Cat-Folch UP | 44 | 28.8 | 50 | 13 | 9 | 0 |
| Porcine-Folch UP | 10 | 18.7 | 80 | 1 | 1 | 0 |
| Ovine-Folch UP | 4 | 18.40 | 100 | 0 | 0 | 0 |
| Dog-Folch UP | 4 | 23.40 | 100 | 0 | 0 | 0 |
| Cat Folch LP | 44 | 33.2 | 41 | 16 | 8 | 2 |
| Porcine Folch LP | 15 | 22.7 | 60 | 6 | 0 | 0 |
| Ovine Folch LP | 4 | 10.00 | 100 | 0 | 0 | 0 |
| Dog Folch LP | 4 | 38.40 | 25 | 3 | 0 | 0 |
| C18 COLUMN ELUATES | | | | | | |
| Cat, C18 Lipid | 4 | 35.05 | 50 | 1 | 1 | 1 |
| Porcine, C18 Lipid | 14 | 25.8 | 64 | 5 | 0 | 0 |
| Cat C18 nonlipid | 8 | 15.88 | 75 | 1 | 1 | 0 |
| Porcine, Lipid UP, base trt | 5 | 18.72 | 80 | 1 | 0 | 0 |
| Cat, Lipid UP base trt | 10 | 38.70 | 20 | 8 | 0 | 0 |
| Cat, C18 nonlipid MeOH sol | 11 | 46.70 | 18 | 9 | 0 | 0 |
| Porcine,C18 nonlipid MeOH | 11 | 40.7 | 18 | 9 | 0 | 0 |
| Porcine, C18 nonlipid H2O | 12 | 27.8 | 42 | 7 | 0 | 0 |
| Cat, C18 nonlipid (sol.) | 10 | 40.1 | 10 | 8 | 1 | 0 |
| DEAE COLUMN | | | | | | |
| Cat, Total Gangs. | 12 | 27.8 | 50 | 3 | 3 | 0 |
| Cat monosialgang. | 18 | 34.1 | 39 | 10 | 1 | 0 |
| Porcine, Monosialogang. | 29 | 23.2 | 62 | 11 | 2 | 2 |
| Cat, disialogang. | 15 | 15.1 | 100 | 0 | 0 | 0 |
| Porcine, disialogang. | 28 | 25.8 | 57 | 10 | 2 | 0 |
| Cat, trisialogang. | 17 | 21.6 | 82 | 3 | 0 | 0 |
| Porcine, trisialogang. | 35 | 30.2 | 49 | 12 | 0 | 0 |
| Cat, Neutral gang. Forssman.. | 49 | 29.0 | 49 | 25 | 0 | 0 |
| Porcine, Neutral Gang. | 14 | 33.4 | 50 | 0 | 0 | 0 |
| Cat, Non-lipid, DEAE neutral | 15 | 23.6 | 67 | 5 | 0 | 0 |
| Cat, Non-lipid, neutral, H2Osol. | 14 | 24.3 | 57 | 6 | 0 | 0 |
| Cat. Nonlipid, neut. MeOH sol. | 14 | 33.8 | 36 | 8 | 1 | 0 |
| Cat, Mono, di,tri-sial gang. | 23 | 38.9 | 13 | 19 | 1 | 0 |
| Porcine, Mono,di, tri-sialo | 26 | 21.8 | 65 | 9 | 0 | 0 |
| Cat, mono, di-sialogang | 9 | 34.1 | 33 | 6 | 0 | 0 |
| Porcine,mono, disialogang. | 18 | 28.6 | 44 | 10 | 0 | 0 |
| Cat, mono, trisialogang. | 16 | 37.6 | 19 | 13 | 0 | 0 |
| Porcine, mono, trisialogang. | 26 | 27.0 | 50 | 13 | 0 | 0 |
| Cat, di, trisialogang. | 8 | 30.9 | 37 | 3 | 2 | 0 |
| Porcine, di,trisialogang. | 27 | 27.0 | 56 | 12 | 0 | 0 |
| Cat, monosialogangl. Forssman | 16 | 20.9 | 87 | 2 | 0 | 0 |
| UNISIL COLUMN | | | | | | |
| CAT, LP, CHCl3 | 22 | 30.0 | 36 | 13 | 1 | 0 |
| Porcine LP, CHCl3 | 9 | 34.1 | 22 | 7 | 0 | 0 |
| CAT, LP, Acetone:MeOH | 39 | 35.1 | 23 | 29 | 1 | 0 |
| Porcine LP, Acetone:MeOH | 12 | 26.7 | 58 | 5 | 0 | 0 |
| Cat, LP, Methanol | 26 | 33.1 | 23 | 20 | 0 | 0 |
| Porcine, LP, Methanol | 11 | 34.0 | 27 | 8 | 0 | 0 |
| IATROBEADS (CHROMATOGRAPHY) | | | | | | |
| FRACTION NO | | | | | | |
| I | 4 | 45 | 0 | 3 | 1 | 0 |
| II | 4 | 15 | 75 | 1 | 0 | 0 |
| III | 4 | 41.75 | 25 | 2 | 1 | 0 |
| IV | 4 | 43.4 | 0 | 4 | 0 | 0 |
| V | 4 | 33.35 | 25 | 2 | 1 | 0 |
| GEL PERMEATION | | | | | | |
| I | 5 | 32.08 | 40 | 4 | 0 | 0 |
| II | 7 | 24.77 | 43 | 3 | 1 | 0 |
| III | 6 | 33.40 | 33 | 2 | 2 | 0 |
| IV | 4 | 29.44 | 80 | 1 | 0 | 0 |
| V | 5 | 25.36 | 60 | 2 | 0 | 0 |
| VI | 5 | 29.40 | 40 | 3 | 0 | 0 |
| VII | 5 | 22.72 | 60 | 2 | 0 | 0 |
| VIII | 6 | 32.27 | 33 | 3 | 1 | 0 |
| IX | 3 | 17.87 | 100 | 0 | 0 | 0 |
| X | 3 | 33.40 | 33 | 1 | 1 | 0 |
| XI | 4 | 40.05 | 25 | 1 | 2 | 0 |
| AFFINITY CHROMATOGRAPHY | | | | | | |
| FRACTION | | | | | | |
| Heparin-binding from Folch UP (cat) | 14 | 29.1 | 50 | 6 | 1 | 0 |
| Heparin-binding from PBS homogenate (FIG. 1) (cat) | 4 | 46.8 | 0 | 3 | 1 | 0 |
| Gelatin-binding from Folch UP (cat) | 4 | 31.7 | 50 | 1 | 1 | 0 |

Table IV, which follows, contains data similar to that in Tables I-III. The samples, however, are all ganglioside materials. The first group is ganglioside obtained from cat omental extracts. The ganglioside were separated into mono, di and tri-sialyated components, and were also mixed, in 1:1, or 1:1:1 ratios. Similar analyses were performed with porcine omenta-derived glycosides.

The "Supelco'" group presents analysis for known, commercially available gangliosides, (entries 1–4 of this group). Entries 5–8, however, represent new compositions of gangliosides.

This table also presents a value for the materials, the "DU" or Discriminator Value.

In order to determine the "DU" value, the A Index value is taken as well as the percent negative Means values $s_I$ and $S_I$ the compounds of a class I, and $s_{II}$ and $S_{II}$ values of a class II. These numbers, $s_I$, $S_I$, $s_{II}$ and $S_{II}$ determine centroids of distribution of each class of compounds. Using this, values $W_1$ and $w_2$ and $X_{1T}$, $X_{2T}$, "weight coefficients" are determined via $$w_1 = s_{II} - s_I \quad X_{1T} = (S_{S11} + S_I)/2$$
$$w_2 = S_{II} - S_I \quad X_{2T} = (S_{11} = S_1)/2$$

$$DU = S \frac{w_1}{(w_1^2 + W_2^2)^{\frac{1}{2}}} + S \frac{w_2}{(w_1^2 + w_2^2)^{\frac{1}{2}}}$$

$$\text{and } T = X_{1T}\left[\frac{w_1}{(w_1^2 + w_2^2)^{\frac{1}{2}}}\right] + X_{2T}\left[\frac{w_2}{(w_1^2 + w_2^2)^{\frac{1}{2}}}\right]$$

The smaller the DU value, the greater the angiogenic properties of the sample. A ranking of DU values by compound, from best to worst is presented in Table V.

TABLE IV

| Compound | Major Component(s) | Eggs | DU | A | % Neg | W | M | S |
|---|---|---|---|---|---|---|---|---|
| Cat Omentum | | | | | | | | |
| Acidic DEAE gangl | | 12 | 39.17 | 27.8 | 50% | 3 | 3 | 0 |
| Monosialogangl. | GM3 | 18 | 26.77 | 34.1 | 39% | 10 | 1 | 0 |
| Disialogangl. | GD3 | 15 | 94.59 | 15.1 | 100% | 0 | 0 | 0 |

TABLE IV-continued

| Compound | Major Component(s) | Eggs | DU | A | % Neg | W | M | S |
|---|---|---|---|---|---|---|---|---|
| Trisialogangl | | 17 | 75.63 | 21.6 | 82% | 3 | 0 | 0 |
| Mono, Di, Tri, (Mix) | | 23 | 0.54 | 38.9 | 13% | 19 | 1 | 0 |
| Mono, Di (Mix) | | 9 | 21.06 | 34.1 | 33% | 6 | 0 | 0 |
| Mono, Tri (Mix) | | 16 | 6.66 | 37.5 | 14% | 13 | 0 | 0 |
| Di, Tri (Mix) | | 8 | 25.84 | 30.9 | 37% | 3 | 2 | 0 |
| Neutral gangl Forssman | | 49 | 37.85 | 29.0 | 49% | 25 | 0 | 0 |
| Mono, Forssman (Mix) | | 16 | 80.67 | 20.9 | 87% | 2 | 0 | 0 |
| Brain GM1 | GM1 | 8 | 23.56 | 38.4 | 37% | 2 | 3 | 0 |
| Brain GM3 | GM3 | 14 | 38.77 | 29.1 | 50% | 6 | 1 | 0 |
| Supelco (Brain) | | | | | | | | |
| Purified Mix Gangl. | | 12 | 21.45 | 32.8 | 33% | 7 | 1 | 0 |
| Monosialogangl. | GM1 | 12 | 47.28 | 26.2 | 58% | 5 | 0 | 0 |
| Disialogangl. | GD1a | 9 | 21.51 | 32.6 | 33% | 6 | 0 | 0 |
| Trisialogangl. | GT1b + GD1b | 18 | 33.67 | 27.1 | 44% | 10 | 0 | 0 |
| Mono/Di (Mix) | | 6 | 19.90 | 37.9 | 33% | 4 | 0 | 0 |
| Mono/Tri (Mix) | | 5 | 93.27 | 21.4 | 100% | 0 | 0 | 0 |
| Di/Tri (Mix) | | 6 | 4.36 | 38.9 | 17% | 5 | 0 | 0 |
| Mono/Di/Tri (Mix) | | 6 | 10.56 | 41.2 | 17% | 4 | 1 | 0 |
| Porcine Omentum | | | | | | | | |
| Monosialogangl | | 29 | 52.0 | 23.2 | 62% | 11 | 2 | 2 |
| Disialogangl | | 28 | 46.44 | 25.8 | 57% | 10 | 2 | 0 |
| Trisialogangl | | 25 | 40.74 | 28.9 | 52% | 12 | 0 | 0 |
| Mono, Di, Tri (Mix) | | 26 | 55.28 | 21.8 | 65% | 9 | 0 | 0 |
| Mono, Di (Mix) | | 18 | 33.21 | 28.6 | 44% | 10 | 0 | 0 |
| Mono, Tri (Mix) | | 26 | 34.41 | 27.0 | 50% | 13 | 0 | 0 |
| Di, Tri (Mix) | | 27 | 45.13 | 27.0 | 56% | 12 | 0 | 0 |

TABLE V

GANGLIOSIDES ANGIOGENIC POTENCY

| RANK | DU | COMPOUND |
|---|---|---|
| 1 | −10.56 | Supelco, Mono/Di/Tri Mixture |
| 2 | 0.54 | Cat Om., Mono/Di/Tri Mixture |
| 3 | 4.36 | Supelco, Di/Tri Mixture |
| 4 | 6.66 | Cat Om., Mono/Tri Mixture |
| 5 | 19.90 | Supelco, Mono/Di Mixture |
| 6 | 21.06 | Cat Om., Mono/Di Mixture |
| 7 | 21.45 | Supelco Purified mixed gangliosides |
| 8 | 21.51 | Supelco Disialo |
| 9 | 23.56 | GM1 |
| 10 | 25.84 | Cat Om., Di/Tri Mixture |
| 11 | 26.77 | Cat Om., Monosialo (GM3) |
| 12 | 33.21 | Porcine Om. Mono/Di Mixture |
| 13 | 33.67 | Supelco Trisialo |
| 14 | 37.85 | Cat Om., Neutral Gangl. Forssman |
| 15 | 38.77 | GM3 |
| 16 | 39.17 | Cat Om., Acidic DEAF gangl |
| 17 | 40.74 | Porcine Om., trisialogangl |
| 18 | 45.13 | Porcine Om., Di/Tri mixture |
| 19 | 46.44 | Porcine Om, Disialogangl |
| 20 | 47.28 | Supelco monosialogangl. |
| 21 | 52.00 | Porcine Om., disialogangl |
| 22 | 55.28 | Porcine Om., Mono/Di/Tri mixture |
| 23 | 75.63 | Cat Om., Trisialogangl. |
| 24 | 80.67 | Cat Om./Mono/Forrsman Mixture |
| 25 | 93.27 | Supelco Mono/Tri Mixture |
| 26 | 94.59 | Cat Om., Disialogangl |

These results show that, while the CMFr does possess angiogenic activity vis a vis the CAM assay, the additional fractionates obtained following the process outlined in FIG. II, possess greater Angiogenic properties. For example, by reference to Table III, Cat CMFr (the first entry) has an A value of 28.98, but 46.34% of the tests were negative. The purer, monosialogangliosides obtained on DEAE column, in contrast, show an A value of 34.1, with only 39% negative. In contrast, non-lipid fractions, also from DEAE columns, show 23.6 and 67% negative—a drop, in spite of purification. Finally, for this comparison, a mix of mono, di, and tri sialogangliosides from Cat omentum shows values of 38.9 and only 13% negative.

Additional comparisons can be drawn from the data in Table III. The DU value, displayed in Tables IV and V, is a useful shorthand for showing actual effectiveness, as it takes into account not only the A value, but the percentage negative. The lower the DU value, the more effective the material tested. Hence, by referring to Table VII, it can be seen that the novel mixture of known gangliosides (Supelco mono-, di- and tri-sialogangliosides), and the fraction containing feline mono-, di-, and tri-sialogangliosides, are the most effective compositions.

Figure 16:
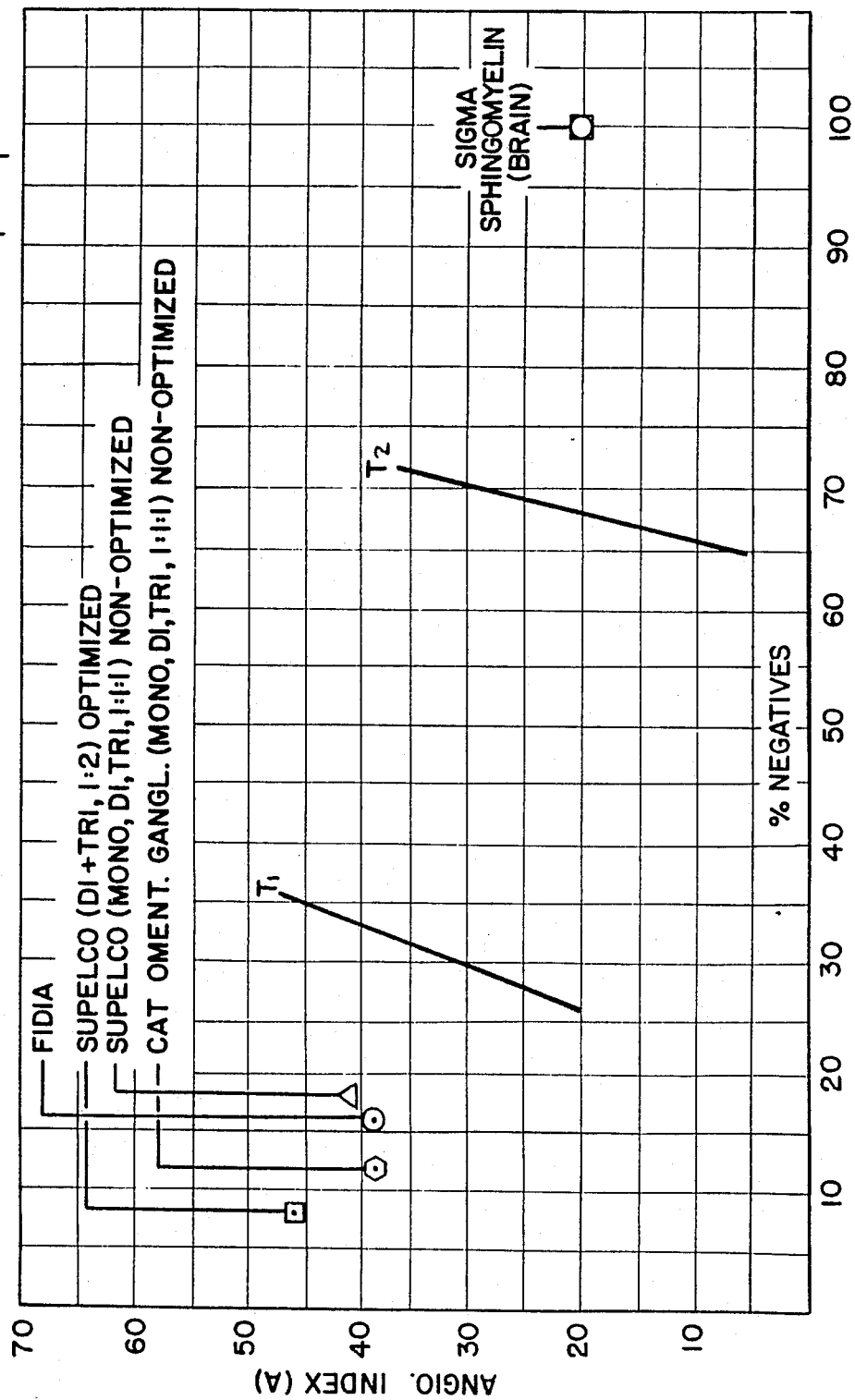

These results may also be shown graphically, as will be seen by referring to FIGS. 6-16. These Figures are linear categorization graphs) for various substances. In linear categorization, as applied herein, Angiogenic Index is platted against the percent negative. A "centroid" or "mean" point is obtained for each group of materials so platted, and the T value is obtained from a comparison of every two groups of compounds. This T value is then an index to which compositions are more effective than others. FIG. III establishes these guidelines for T values, using all samples tested. Subsequently, in FIGS. 7-16 different groups are plotted against the T values. Anything plotting to the left of $T_2$ shows promise as an angiogenic composition. FIG. 16 shows the best compositions.

Figure 17:
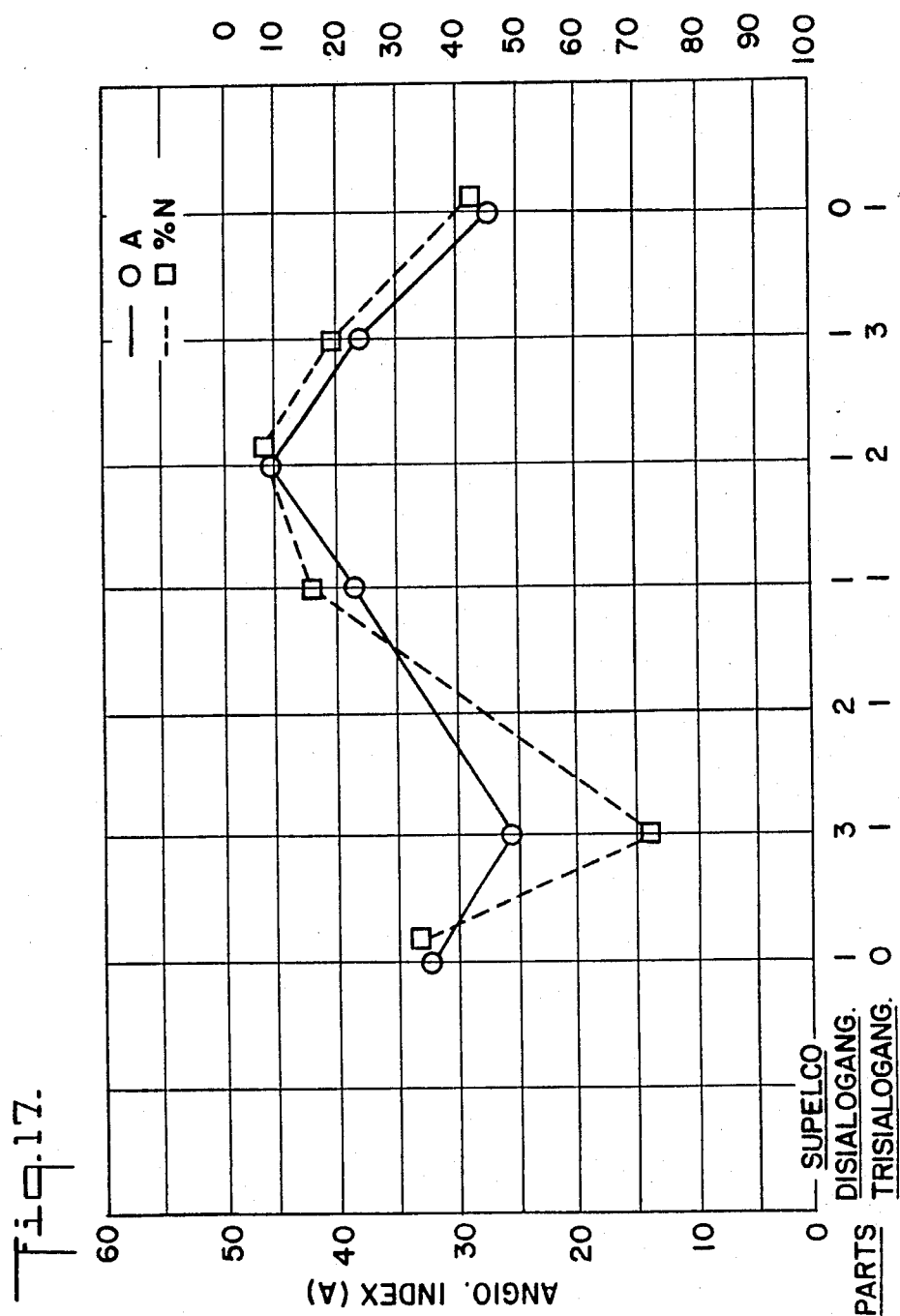

FIG. 17 is included to show a graph of the Angiogenic index plotted against an inverted negative percentage standard, using novel mixtures of known di- and trisialogangliosides. The graph demonstrates that the best mixture is di- and tri-sialogangliosides, in a 1:2 ratio. This graph is interesting because the curves obtained are strinkingly similar to those obtained, when antigen-antibody complexing is plotted. This suggests that a complexing reaction not unlike precipitant and agglutination type reactions characteristic of antigen-antibody systems is taking place.

The following experiments show that the CMFr, described supra, has in vivo efficacy in angiogenesis. The experiments are reported in Ser. No. 672,624, filed Aug. 20, 1984. As will be seen, by reference to Tables III–VII, the CMFr has a lower Angiogenic Index, and a higher Discrimination Unit value than do the additional fractions and mixtures tested in similar fashion (i.e., the CAM assay). One skilled in the art will see, therefore, that it would be expected that these experiments may be repeated with the additional fractions, with expected superior results.

Other commercially available lipid compounds purchased primarily from the Supelio and Sigma Chemical companies, or supplied by individual investigators were tested for the ability to induce angiogenesis in the CAM. These results are presented in Table VI.

TABLE VI

| GLYCOLIPIDS AND GANGLIOSIDES | | | | | | |
|---|---|---|---|---|---|---|
| COMPOUND | EGGS | A | % NEG | W | M | S |
| Cerebrosides (Supelco) | 16 | 36.3 | 38 | 9 | 1 | 0 |
| Gangliosides (Fidia Cronassial 20) | 18 | 38.6 | 17 | 14 | 1 | 0 |
| Gangliosides (Supelco) | 15 | 34.3 | 33 | 8 | 2 | 0 |
| Globoside (Supelco) | 17 | 34.6 | 29 | 10 | 2 | 0 |
| Steryl glucoside (Supelco) | 16 | 43.0 | 19 | 11 | 2 | 0 |
| Ceramides (Supelco) | 17 | 32.2 | 41 | 8 | 2 | 0 |
| Digalactosyl-diglyceride (Supelco) | 14 | 37.2 | 29 | 10 | 0 | 0 |
| Monogalactosyl diglyceride (Supelco) | 4 | 27.6 | 43 | 4 | 0 | 0 |
| Ceramide galactoside (Supelco) | 20 | 27.0 | 60 | 7 | 1 | 0 |
| Purified mixed gangliosides (Supelco) | 19 | 28.8 | 42 | 10 | 1 | 0 |
| Ceramides, Type III (Sigma) | 18 | 31.9 | 44 | 10 | 0 | 0 |
| Cerebrosides, Type I (Sigma) | 19 | 30.2 | 53 | 8 | 1 | 0 |
| Ceramides, Type IV (Sigma) | 16 | 30.5 | 37 | 10 | 0 | 0 |
| Cerabrosides, Type II (Sigma) | 13 | 30.3 | 38 | 8 | 0 | 0 |
| Sulfatides (Sigma) | 7 | 28.7 | 57 | 3 | 0 | 0 |
| Sulfatides (Supelco) | 6 | 30.0 | 50 | 3 | 0 | 0 |
| Glucocerebrosides (Sigma) | 7 | 26.7 | 43 | 4 | 0 | 0 |
| Ceramide trihexoside (Supelco) | 4 | 38.4 | 25 | 3 | 0 | 0 |
| Steryl glucoside (Supelco) | 6 | 46.8 | 0 | 5 | 1 | 0 |
| GM1 | 8 | 38.4 | 37 | 2 | 3 | 0 |
| GM1 purified | 15 | 32.5 | 27 | 11 | 0 | 0 |
| GM3 | 14 | 29.1 | 50 | 6 | 1 | 0 |
| GM3 Purified | 17 | 29.1 | 47 | 8 | 1 | 0 |
| Made-up mixture GM1:GM3 (1:1) purified | 18 | 36.7 | 33 | 11 | 1 | 0 |
| PHOSPHOLIPIDS | | | | | | |
| Phosphatidyl-inositol (Sigma) | 10 | 28.7 | 60 | 4 | 0 | 0 |
| Sphingomyelin (brain) (Sigma) | 8 | 20.9 | 100 | 0 | 0 | 0 |
| Phosphatidylcholine (Sigma) | 10 | 33.4 | 40 | 6 | 0 | 0 |
| Phosphatidylinositol (Supelco) | 6 | 29.0 | 67 | 2 | 0 | 0 |
| Phosphoinositides (Sigma) | 3 | 31.1 | 33 | 2 | 0 | 0 |
| Phosphatidylinositol 4,5 diphosphate (Sigma) | 7 | 31.5 | 43 | 4 | 0 | 0 |
| Phosphatidyl inositol 4-monophosphate (Sigma) | 6 | 28.9 | 50 | 3 | 0 | 0 |
| Sphingomyelin (egg yolk) | 6 | 22.2 | 83 | 1 | 0 | 0 |
| Lysophosphatidyl choline stearoyl (Sigma) | | | 100% death rate | | | |
| NEUTRAL LIPIDS | | | | | | |
| NEUTRO LIPIDS | | | | | | |
| Mono, Di, and Tristearin (1:1:1) (Sigma) | 3 | 20 | 67 | 1 | 0 | 0 |
| Mono, Di, Triolein (1:1:1) (Sigma) | 2 | 0 | 100 | 0 | 0 | 0 |
| Tristearin (Sigma) | 21 | 36.5 | 43 | 8 | 3 | 1 |

TABLE VI-continued

| Triolein (Sigma) | 4 | 45 | 25 | 0 | 3 | 0 |
|---|---|---|---|---|---|---|
| Monostearin (Sigma) | 4 | 50.0 | 0 | 2 | 2 | 0 |
| Monoolein | 4 | 50.0 | 0 | 2 | 2 | 0 |
| Distearin (Sigma) | 3 | 26.7 | 67 | 0 | 1 | 0 |
| Diolein (Sigma) | 3 | 13.3 | 100 | 0 | 0 | 0 |
| Tripalmitin (Sigma) | 4 | 5 | 100 | 0 | 0 | 0 |
| Cholesterol palmitate (Sigma) | 3 | 0 | 100 | 0 | 0 | 0 |
| Triarachidin (Sigma) | 4 | 41.7 | 0 | 4 | 0 | 0 |
| Paraffin oil (Fisher) | 4 | 40 | 0 | 4 | 0 | 0 |
| STEROIDS | | | | | | |
| Ergosterol (Supelco) | 14 | 37.7 | 36 | 6 | 3 | 0 |
| Desmosterol (Supelco) | 4 | 26.7 | 50 | 2 | 0 | 0 |
| Lanosterol (Supelco) | 8 | 28.4 | 38 | 5 | 0 | 0 |
| Stigmasterol (Supelco) | 6 | 37.9 | 33 | 4 | 0 | 0 |

One skilled in the art will see that additional tissues, characterized by the presence of lipid containing molecules, may be analyzed in this fashion to obtain potentially active fractions lipid containing mammalian tissues, such as the liver, brain, epithelial tissue, and so forth, as well as plant tissues, especially seeds. Plants are known as good sources of lecithins, and angiogenically active lecithins may be found. Synthetically produced lipids may be used also.

A set of experiments was performed to demonstrate the neovascularization effects of the non-aqueous lipid preparation at a site where the normal vascularization in the tissue was purposely destroyed. Adult female cats were anesthetized with an intramuscular injection of Ketamine using a dosage of 7 ml/Kg. Each cat was placed in a supine position and an incision made between the knee and the inguinal crease of both hind legs. The femoral arteries were isolated, ligated, and removed between the groin and the first deep femoral branch (Hunter's canal). The incision was closed and each cat subjected immediately to an intravenous injection of stannous chloride/Technitium-99 which attaches to and radioactively labels the red blood cells in the tissue. The location and quantity of this radionuclide can be identified using a Gamma camera scan. In this matter, blood vessels and capillaries carrying the radioactively tagged red blood cells are specifically visualized.

The stannous chloride/phosphate preparation contained 10 mg of sodium pyrophosphate, 30 mg of sodium trimetaphosphate, and 0.95 mg stannous chloride. This preparation was reconstituted by adding 2.0 ml of PBS and 1.0 ml of this solution was injected intravenously into the bronchial vein of the cat. Twenty minutes later, an intravenous dose of 10 m Curries of Technisium-99 m was injected to radiolabel the red blood cells in that tissue area. Nuclear imaging scanning and digital integration of blood flow was observed and followed.

After the cats had been surgically prepared, a "baseline" scan for background radioactivity of the surgical sites was made, followed by injection of between 6–7 ml of the chloroform/methanol extracted and evaporated viscous liquid lipid suspended in PBS intramuscularly in equal amounts into two preselected and marked sites on the right leg in the area where the femoral artery was removed. A placebo injection containing only PBS was made into two similarly identified and marked sites on the left leg. Under normal circumstances, the recognized response of the body to this kind of surgery will be to try and establish collateral blood circulation to the injured tissues by forming new capillaries and blood vessels in the area where the femoral artery was severed. By following and comparing the rate and degree of new blood circulation in each leg following the surgery, a direct and verifiable assessment of the angiogenic properties and potency of the chloroform/methanol extracted lipid preparation was accurately made.

Figure 19:
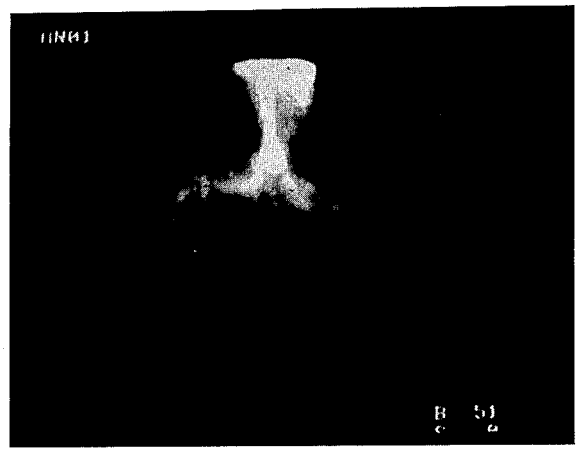
Figure 20:
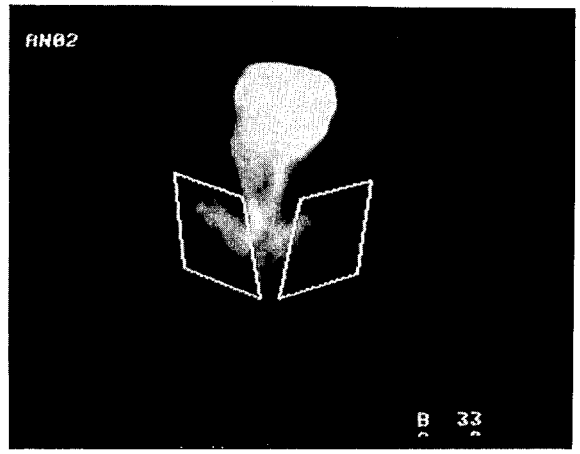
Figure 21:
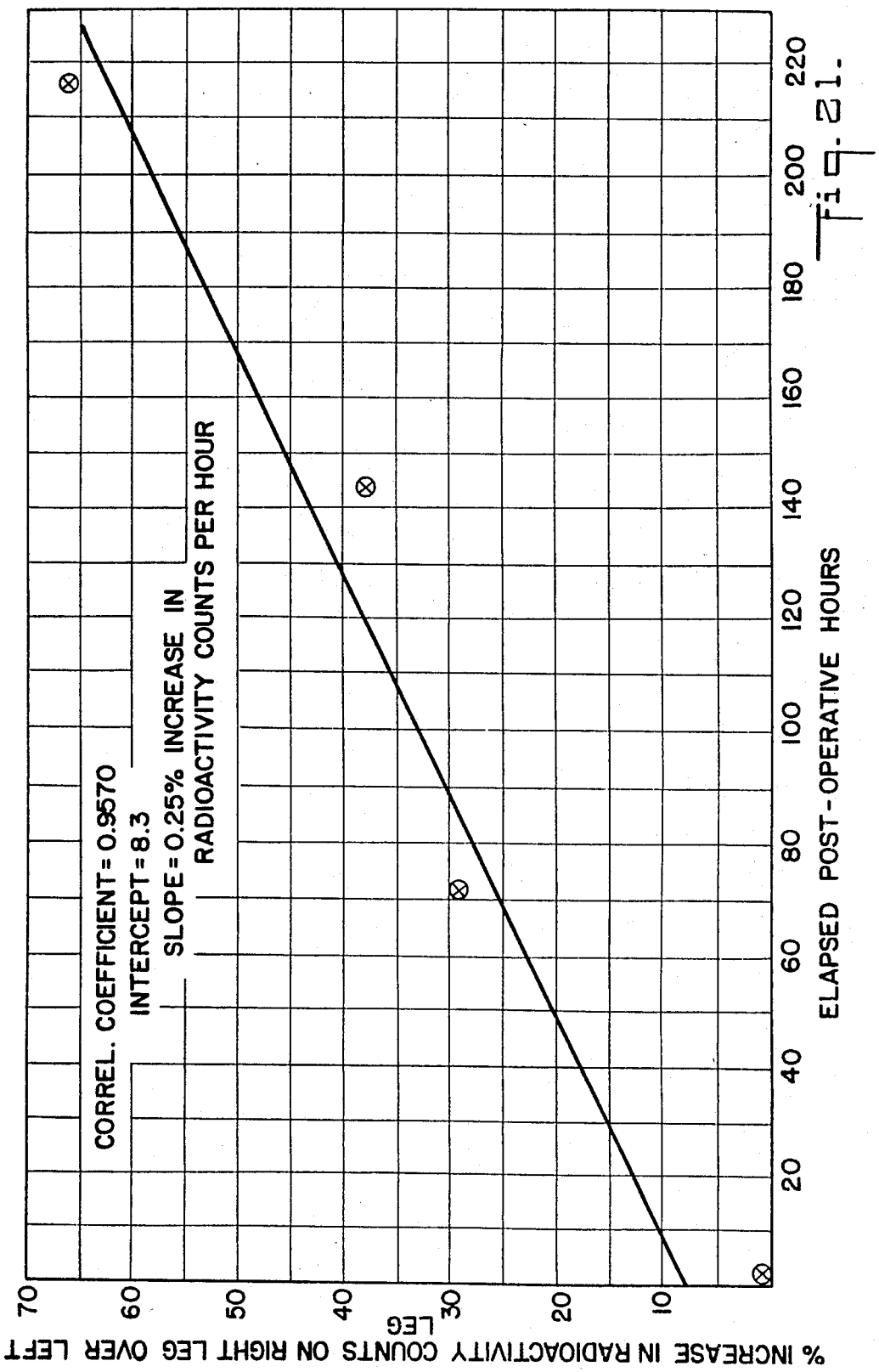

Subsequent intravenous injection of the stannous chloride/Technitium-99 m preparation was made into the preselected sites on each leg and each leg was subjected to nuclear scan at three, six, and nine days after the operation. The results of these nuclear scans are shown in FIGS. 18-20 which exemplify the effects of the lipid fraction for neovascularization in a representative cat. The data shows that the increase in blood vessel formation in the right leg of this cat (injected with the omental lipid preparation) and substantially higher integrated radioactivity counts then the left (control) leg. At seventy-two hours post surgery, a 29.6% difference in radioactivity was observed; at six days post operative time, a 38.2% increase in radioactivity was observed in the right leg in comparison to the left; and after nine days the rate of neovascularization in the right leg showed a 65.8% increase over that in the left leg. The photographs of FIGS. 18-20 provide visual evidence of the substantial differences in new blood vessel formation using the chloroform/methanol extracted lipid fraction. A graph illustrating a linear increase of radioactivity (in counts) comparing the lipid injected leg vascularization to the vascularization of the saline injected leg is provided in FIG. 21. The data reveals a rate of 0.25% per hour increase of neovascularization in the right leg compared to the left. This clearly shows the angiogenic effect of the lipid fraction as evidenced by the substantial increase in new blood vessel formation and vascular organization and structure in the right leg. This data however, overlooks the possibility of a common systemic effect by using the lipid extract preparation which was shown to be in effect by the following additional control experiment.

In this additional control, another cat was surgically operated upon to remove the femoral arteries as described above. But, in this instance, no injection of any kind was given. Gamma camera scans made at three and six day intervals post operatively are shown in FIGS. 22-24. The scan of the right and the left leg is shown in FIG. 22 in which no discernable difference in new blood vessel collateral circulation is visible after three days duration. FIG. 23 shows an anterior view of one leg on the sixth day post surgery and FIG. 24 shows the posterior view on the same day. The scane indicated no difference in counts between the two legs at any time post surgery and a much lesser degree of neovascularization in comparison to the earlier experiment. In fact, the neovascularization was noticeably less in this additional experiment than in the left (control) leg in the earlier work. In view of this and the fact that in the previous experiment that the left leg of the cat (injected control) exhibited a relatively higher degree of neovascularization (although substantially lesser than in the right leg), there is a basis for believing that part of the lipid preparation in the right leg was probably transferred systemically to the left leg in the earlier experiments.

The in vivo experiments, using CMFr, may be repeated with the different materials obtained following hexane/ethanol extraction. As a comparison between these fractions and CMFr may be made from the data in Tables III-VII, supra, one skilled in the art will conclude that these purified extracts would result in even more rapid, and better angiogenesis. Compositions which possess angiogenically active lipid containing molecules have been obtained from mammalian tissues. The compositions, in therapeutically effective amounts, have been shown to affect angiogenic activity in a way not previously expected. Tissues similar to omentum, such as lipid containing mammaliam tissue and plant tissue, may be expected to have angiogenically active molecules as well. Synthetic lipids, based upon the structures of the molecules shown to be angiogenically active, are foreseen as well.

In practice, the compositions can be administered in any of the standard ways known to the art, including intravenously, intramuscularly, orally, and topically. The amount, or dose, will of course vary from patient to patient.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A process for obtaining a composition with enhanced angiogenic acitivity comprising containing a sample of mammalian tissue with a first solvent under conditions favoring extraction of angiogenically active lipid containing molecules selected from the group consisting of phospholipids, ceramides, cerebrosides, neutral lipids, triglycerides, diglycerides, monoglycerides lecithin and sphingosides into said first solvent and further contacting said angiogenically active lipid containing first solvent with a second solvent under conditions favoring extraction of said angiogenically active lipid containing molecules but not angiogenic inhibiting substances, said first and second solvents being insoluble in each other.

2. A process as in claim 1, wherein said first solvent is a chloroform-methanol mixture.

3. A process as in claim 1, wherein said second solvent is a hexane ethanol mixture.

4. A process as in claim 1, wherein said first solvent is a chloroform-methanol mixture and said second solvent is a hexane-ethanol mixture.

5. Process as in claim 1, wherein said angiogenically active lipid-containing second solvent is separated into component hexane and ethanol phases.

6. Process as in claim 5, wherein said ethanol phase is partitioned into an upper and a lower phase by combining with a mixture of chloroform, methanol, and water.

7. Process as in claim 6, wherein said upper phase is separated into two phases by combining said upper phase, in sequence, with a mixture of methanol and water, and a mixture of chloroform and methanol.

8. A process as in claim 6, wherein said lower phase is mixed, sequentially, with chloroform, acetone, and methanol, to form three separate portions.

9. Method as in claim 6, wherein said lower phase is contacted with separate portions of chloroform, acetone, and methanol to form separate fractions thereof.

10. Process of claim 6, wherein said upper phase is further contacted with a first mixture of methanol and water and a second mixture of chloroform and methanol to form a solvent of chloroform and methanol containing said angiogenically active lipid containing molecules but not non-lipid containing molecules.

11. Process of claim 10, further comprising contacting said solvent with a solvent mixture of chloroform methanol and water to obtain non-ganglioside angiogenically active lipid containing molecules.

12. A method of enhancing angiogenesis in a patient comprising applying to said patient a therapeutically effective amount of a composition containing an angiogenically active lipid containing molecule selected from the group consisting of a phospholipid, a ceramide, a cerebroside, a neutral lipid, a triglyceride, a diglyceride, amonoglyceride, a lecithin, and a sphingoside.

13. Method of claim 4, wherein said composition is applied orally, intravenously, or topically.

14. The method of claim 12, wherein said angiogenically active lipid containing molecule is a phospholipid.

15. The method of claim 12, wherein said angiogenically active lipid containing molecule is a ceramide.

16. The method of claim 12, wherein said angiogenically active lipid containing a molecule is a cerebroside.

17. The method of claim 12, wherein said angiogenically active lipid containing molecule is a neutral lipid.

18. The method of claim 12, wherein said angiogenically active lipid containing molecule is a triglyceride.

19. The method of claim 12, wherein said angiogenically active lipid containing molecule is a diglyceride.

20. The method of claim 12, wherein said angiogenically active lipid containing molecule is a monoglyceride.

21. The method of claim 12, wherein said angiogenically active lipid containing molecule is a lecithin.

22. The method of claim 12, wherein said angiogenically active lipid containing molecule is a sphingoside.

* * * * *